(12) United States Patent
Feng et al.

(10) Patent No.: US 8,669,369 B2
(45) Date of Patent: Mar. 11, 2014

(54) METHOD AND PROCESS FOR PREPARATION AND PRODUCTION OF DEUTERATED Ω-DIPHENYLUREA

(75) Inventors: Weidong Feng, Jiangsu (CN); Xiaoyong Gao, Jiangsu (CN); Xiaojun Dai, Jiangsu (CN)

(73) Assignee: Suzhou Zelgen Biopharmaceutical Co., Ltd., Jiangsu (CN)

( * ) Notice: Subject to any disclaimer, the term of this patent is extended or adjusted under 35 U.S.C. 154(b) by 0 days.

(21) Appl. No.: 13/635,822

(22) PCT Filed: Mar. 17, 2011

(86) PCT No.: PCT/CN2011/071926
§ 371 (c)(1),
(2), (4) Date: Sep. 18, 2012

(87) PCT Pub. No.: WO2011/113367
PCT Pub. Date: Sep. 22, 2011

(65) Prior Publication Data
US 2013/0035492 A1 Feb. 7, 2013

(30) Foreign Application Priority Data
Mar. 18, 2010 (CN) .......................... 2010 1 0127706

(51) Int. Cl.
*C07D 213/63* (2006.01)
*C07C 209/68* (2006.01)
*C07D 207/408* (2006.01)
*C07D 213/81* (2006.01)

(52) U.S. Cl.
USPC ............ 546/298; 546/323; 548/545; 564/487

(58) Field of Classification Search
None
See application file for complete search history.

(56) References Cited

U.S. PATENT DOCUMENTS

2009/0069388 A1    3/2009   Czarnik

FOREIGN PATENT DOCUMENTS

| CN | 101676266 A | 3/2010 |
| WO | 0042012 A1 | 7/2000 |
| WO | 2009034308 A2 | 3/2009 |
| WO | 2009054004 A2 | 4/2009 |

OTHER PUBLICATIONS

Int'l Search Report issued Jun. 23, 2011 in Int'l Application No. PCT/CN2011/071926.
Wilhelm et al, "BAY 43-9006: Preclinical Data", Current Pharmaceutical Design, vol. 8, pp. 2255-2257 (2002).

*Primary Examiner* — Janet L Andres
*Assistant Examiner* — Timothy R Rozof
(74) *Attorney, Agent, or Firm* — Panitch Schwarze Belisario & Nadel LLP

(57) ABSTRACT

Methods and processes for preparation and production of deuterated ω-diphenylurea are disclosed. Especially, a kind of deuterated ω-diphenylurea compounds which can inhibit phosphokinase and the preparation method of N-(4-chloro-3-(trifluoromethyl)phenyl)-N'-(4-(2-(N-d3-methylcarbamoyl)-4-pridinyloxy)phenyl)urea are disclosed. The said deuterated diphenylurea compounds can be used for treating or preventing tumors and relative diseases.

7 Claims, 1 Drawing Sheet

METHOD AND PROCESS FOR PREPARATION AND PRODUCTION OF DEUTERATED Ω-DIPHENYLUREA

CROSS-REFERENCE TO RELATED APPLICATION

This application is a Section 371 of International Application No. PCT/CN2011/071926, filed Mar. 17, 2011, which was published in the Chinese language on Sep. 22, 2011, under International Publication No. WO 2011/113367 A1 the disclosure of which is incorporated herein by reference.

FIELD OF INVENTION

This invention relates to the field of chemical synthesis, and particularly relates to the methods and processes for preparation and production of deuterated ω-diphenylurea.

BACKGROUND OF INVENTION

Ω-diphenylurea derivatives are known compounds with c-RAF kinase inhibition activity. For example, WO2000/042012 had disclosed a class of ω-carboxyl-aryl-substituted diphenylurea and the use thereof for treating cancer and related diseases.

Initially, ω-diphenylurea compounds, such as Sorafenib, were firstly found as the inhibitor of c-RAF kinase. The other studies had shown that they could also inhibit the MEK and ERK signal transduction pathways and activities of tyrosine kinases including vascular endothelial growth factor receptor-2 (VEGFR-2), vascular endothelial growth factor receptor-3 (VEGFR-3), and platelet-derived growth factor receptor-β (PDGFR-β) (Curr Pharm Des 2002, 8, 2255-2257). Therefore, they were called multi-kinase inhibitors that resulted in dual anti-tumor effects.

Sorafenib (trade name Nexavar), a novel oral multi-kinase inhibitor, was developed by Bayer and Onyx. In December 2005, based on its excellent performance in phase III clinical trials for advanced renal cell carcinoma, Sorafenib was approved by FDA for treating advanced renal cell carcinoma, and marketed in China in November 2006. However, Sorafenib has various side-effects, such as hypertension, weight loss, rash and so on.

However, novel compounds with raf kinase inhibition activity or better pharmacodynamic properties and the preparation process thereof are still needed to be developed.

SUMMARY OF INVENTION

The object of the invention is to provide novel compounds with raf kinase inhibition activity and better pharmacodynamic properties and the uses thereof.

Another object of the invention is to provide a series of methods to prepare deuterated ω-diphenylurea and the intermediates thereof, thereby meeting the production guidances in the pharmaceutical industry and improving the operability and safety.

In the first aspect, the invention provides a deuterated ω-diphenylurea compound or the pharmaceutical acceptable salts thereof, wherein said compound is N-(4-chloro-3-(trifluoromethyl)phenyl)-N'-(4-(2-(N-(methyl-d$_3$)aminoformyl)-4-pyridyl oxy)phenyl)urea;

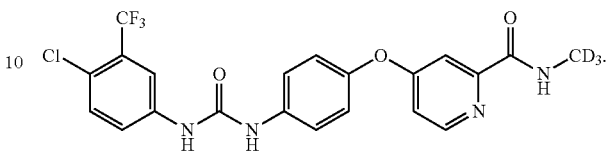

In one embodiment, N in said compound is $^{14}$N.

In the second aspect, the invention provides a method for preparing N-(4-chloro-3-(trifluoromethyl)phenyl)-N-(4-(2-(N-(methyl-d$_3$)aminoformyl)-4-pyridyl oxy)phenyl)urea,

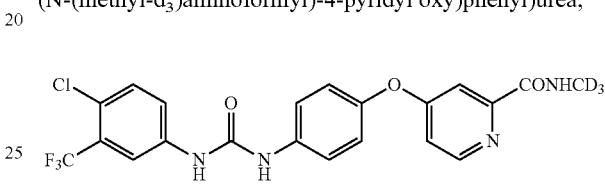

comprising:

(a) in an inert solvent and in the presence of a base, reacting compound III with compound V to form said compound;

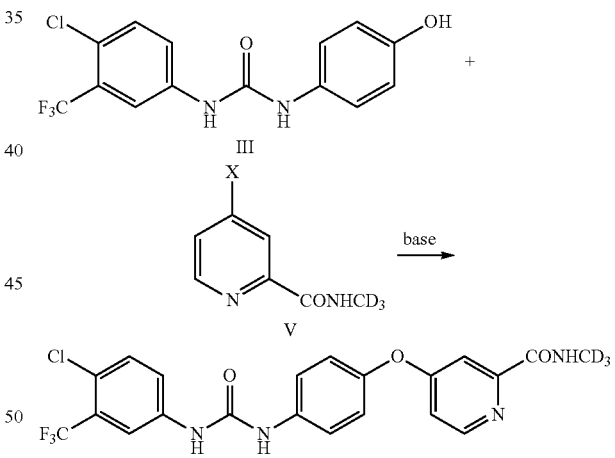

wherein, X is Cl, Br, or I;

or, comprising:

(b) in an inert solvent, reacting compound IX with CD$_3$NH$_2$ or CD$_3$NH$_2$·HCl to form said compound:

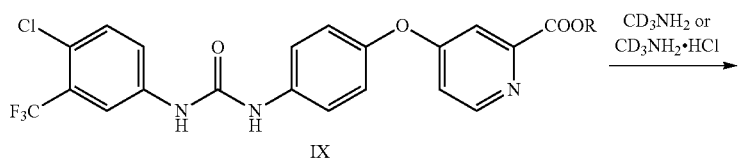

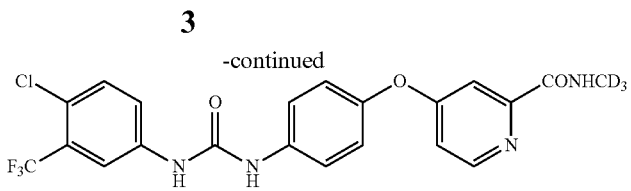

wherein, R is straight-chain or branched chain C1-C8 alkyl, or aryl;

or comprising:

(c) in an inert solvent, reacting 4-chloro-3-trifluoromethyl phenyl isocyanate (VIII) with compound 5 to form said compound;

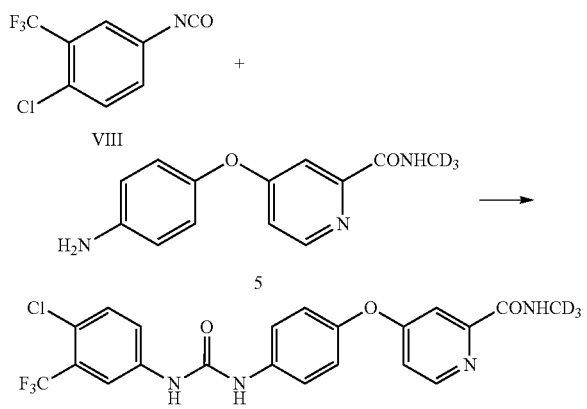

or comprising:

(d) in an inert solvent and in the presence of CDI and $CH_2Cl_2$, reacting compound with compound 6 to form said compound.

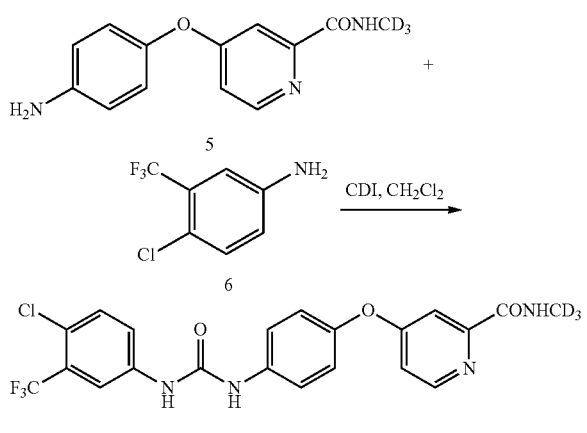

In one embodiment, compound III is prepared as follows:

(i) condensing 4-hydroxy-aniline (I) with 4-chloro-3-trifluoromethyl-aniline (II) to form compound III.

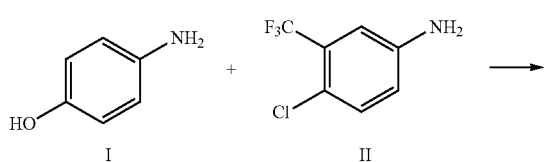

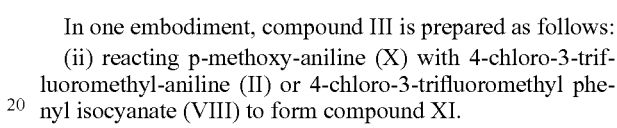

In one embodiment, compound III is prepared as follows:

(ii) reacting p-methoxy-aniline (X) with 4-chloro-3-trifluoromethyl-aniline (II) or 4-chloro-3-trifluoromethyl phenyl isocyanate (VIII) to form compound XI.

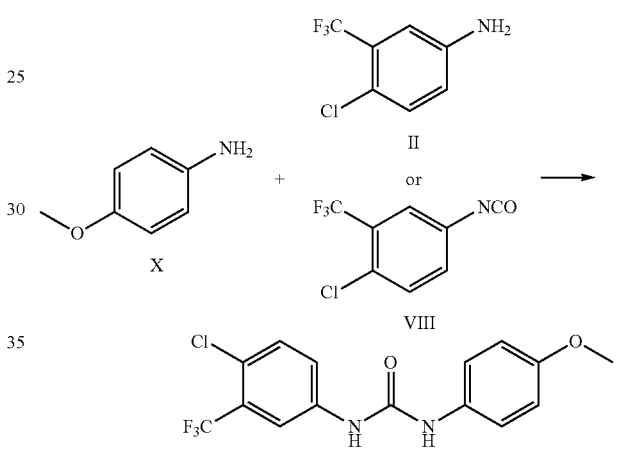

and then, in an acidic or basic condition, demethylation of compound XI to give compound III.

In one embodiment, compound VII is prepared as follows:

In the presence of a base, reacting compound VI and p-hydroxyl-aniline to form compound VII:

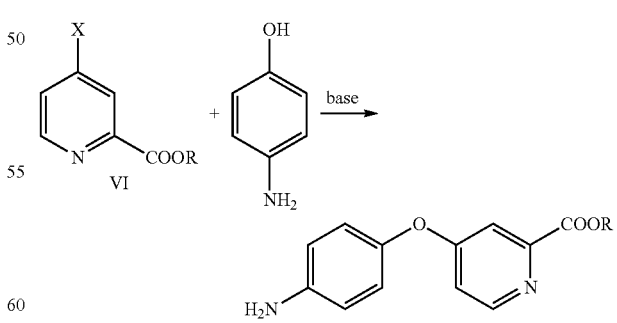

wherein, X is chlorine, bromine or iodine; R is straight-chain or branched chain C1-C8 alkyl, or aryl.

In one embodiment, said base is selected from potassium tert-butoxide, sodium hydride, potassium hydride, potassium carbonate, cesium carbonate, potassium phosphate, potassium hydroxide, sodium hydroxide or the combination thereof.

In one embodiment, the method (a) further comprises that the reaction is conducted in the presence of a catalyst, wherein said catalyst is selected from CuI and proline; or CuI and picolinate.

In one embodiment, the reaction temperature is 0-200° C.

In the third aspect, the invention provides an intermediate as formula B,

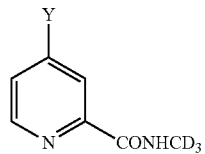

(B)

wherein, Y is halogen or

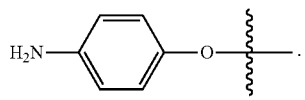

In one embodiment, Y is Cl, and the structure of formula B is

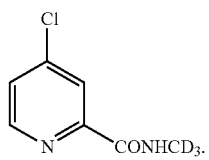

In the fourth aspect, the invention provides a method for preparing 4-chloro-N-(methyl-$d_3$)picolinamide, which comprises:

(a1) under a basic condition and in an inert solvent, reacting methyl 4-chloropicolinate with (methyl-$d_3$)amine or salts thereof to form 4-chloro-N-(methyl-$d_3$)picolinamide; or (a2) in an inert solvent, reacting 4-chloropicolinoyl chloride with (methyl-$d_3$)amine to form 4-chloro-N-(methyl-$d_3$)picolinamide.

In one embodiment, said inert solvent includes tetrahydrofuran, ethanol, methanol, water, or the mixture thereof.

In one embodiment, in step (a1) and (a2), the reaction temperature is −10° C. to reflux temperature, preferably is −4° C. to 60° C., and more preferably is 5-50° C.

In one embodiment, in step (a1) and (a2), the reaction time is 0.5-72 hours, preferably is 1-64 hours, and more preferably is 2-48 hours.

In one embodiment, in step (a1), said basic condition means that potassium carbonate, sodium carbonate, cesium carbonate, KOH, NaOH, or the combination thereof is present in the reaction system.

In the fifth aspect, the invention provides a method for preparing 4-(4-aminophenoxy)-N-(methyl-$d_3$)picolinamide, which comprises:

under a basic condition and in an inert solvent, reacting 4-chloro-N-(methyl-$d_3$)picolinamide with 4-amino-phenol to form 4-(4-aminophenoxy)-N-(methyl-$d_3$)picolinamide.

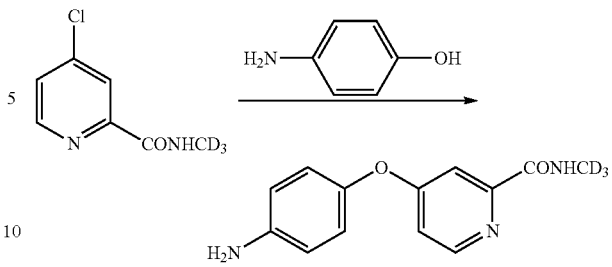

In one embodiment, said basic condition means that KOH, NaOH, potassium carbonate, sodium carbonate, cesium carbonate, potassium tert-butoxide, sodium tert-butoxide or the combination thereof is present in the reaction system.

In one embodiment, said inert solvent is selected from DMF, DMSO, N,N-dimethylacetylamide, tetrahydrofuran, methylpyrrolidin-2-one, 1,4-dioxane, or the mixture thereof.

In one embodiment, the reaction temperature described above is 0° C. to 160° C., preferably is 20° C. to 120° C., and more preferably is 30-100° C.

The reaction time is 0.5-48 hours, preferably is 1-36 hours, and more preferably is 3-24 hours.

In the fifth aspect, the invention provides the use of said intermediates according to the third aspect of the invention for preparing deuterated ω-diphenylurea or as the the starting material for preparing deuterated ω-diphenylurea.

In one embodiment, said deuterated diphenylurea includes 4-(4-(3-(4-chloro-3-(trifluoromethyl)phenyl]ureido)-phenoxy)-N-(methyl-$d_3$)picolinamide (CM4307); and 4-(4-(3-(4-chloro-3-(trifluoromethyl)phenyl]ureido)-phenoxy)-N-(methyl-$d_3$)picolinamide p-toluenesulfonate (CM4307•TsOH).

It should be understood that in the present invention, any of the technical features specifically described above and below (such as in the Examples) can be combined with each other, thereby constituting new or preferred technical solutions that are not described one by one in the specification.

DETAILED DESCRIPTION OF INVENTION

Figure 1:
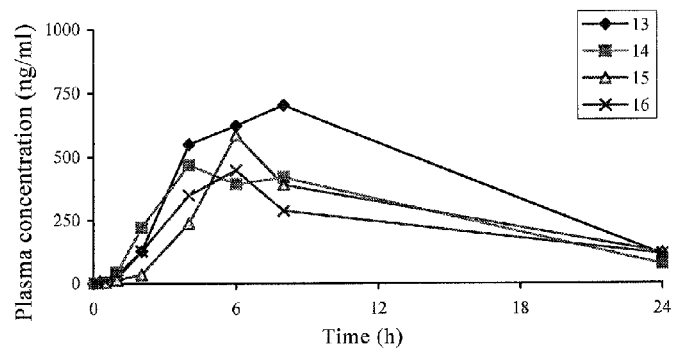
FIG. 1 shows the curves of drug concentration (ng/ml) in plasma after oral adminstration of 3 mg/kg of the control compound CM4306 to the male SD rats.

After studies, the inventors unexpectedly discovered that, compared with the un-deuterated compound, the deuterated ω-diphenylurea of the invention and the pharmaceutically acceptable salts thereof possessed better pharmacokinetic and/or pharmacodynamic properties. Therefore, they were much more suitable as raf kinases inhibitors for preparing medicaments to treat cancer and the relevant diseases.

Moreover, the inventors also discovered that diphenylurea compounds could be efficiently and readily prepared using the new intermediate of formula B,

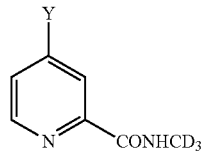
(B)

wherein Y is halogen or

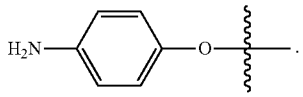

Based on this discovery, the inventors completed the present invention.

DEFINITION

As used herein, the term "halogen" refers to F, Cl, Br and I. Preferably, halogen is selected from F, Cl, and Br.

As used herein, the term "alkyl" refers to straight-chain or branched chain alkyl. Preferably, alkyl is C1-C4 alkyl, such as methyl, ethyl, propyl, iso-propyl, butyl, iso-butyl, tert-butyl and so on.

As used herein, the term "deuterated" means that one or more hydrogen in the compound or group is substituted by deuterium. "Deuterated" can be mono-substituted, bi-substituted, multi-substituted or total-substituted. The terms "one or more deuterium-substituted" and "substituted by deuterium once or more times" can be used interchangeably.

In one embodiment, the deuterium content in a deuterium-substituted position is at least greater than the natural abundance of deuterium (0.015%), preferably >50%, more preferably >75%, more preferably >95%, more preferably >97%, more preferably >99%, more preferably >99.5%.

In one embodiment, the compound of formula (I) comprises at least one deuterium atom, preferably three deuterium atoms, and more preferably five deuterium atoms.

As used herein, the term "compound CM4306" is 4-(4-(3-(4-chloro-3-(trifluoromethyl)phenyl]ureido)-phenoxy)-N-methylpicolinamide.

As used herein, the term "compound CM4307" is 4-(4-(3-(4-chloro-3-(trifluoromethyl)phenyl]ureido)-phenoxy)-N-(methyl-d$_3$)picolinamide.

As used herein, the term "TsOH" represents p-toluenesulfonic acid. Therefore, CM4307•TsOH represents the p-toluenesulfonate of CM4307.

Deuterium-Substituted ω-diphenylurea

The preferred deuterium-substituted ω-diphenylurea compounds according to the invention have the structure of formula (I):

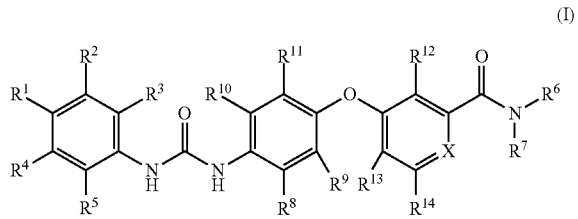
(I)

wherein,

X is N or N$^+$—O$^-$;

R$^1$ is halogen (such as F, Cl or Br), one or more deuterium-substituted or perdeuterated C1-C4 alkyl;

R$^2$ is non-deuterated C1-C4 alkyl, one or more deuterium-substituted or perdeuterated C1-C4 alkyl, or partly or totally halogen-substituted C1-C4 alkyl;

each of R$^3$, R$^4$, R$^5$, R$^8$, R$^9$, R$^{10}$, R$^{11}$, R$^{12}$, R$^{13}$ and R$^{14}$ is independently hydrogen, deuterium, or halogen (such as F, Cl or Br);

R$^6$ is hydrogen, deuterium or one or more deuterium-substituted or perdeuterated C1-C4 alkyl;

R$^7$ is hydrogen, deuterium or one or more deuterium-substituted or perdeuterated C1-C4 alkyl;

provided that at least one of R$^2$, R$^3$, R$^4$, R$^5$, R$^6$, R$^7$, R$^8$, R$^9$, R$^{10}$, R$^{11}$, R$^{12}$, R$^{13}$ or R$^{14}$ is deuterated or is deuterium.

In one embodiment, the deuterium content at a deuterium-substituted position is at least greater than the natural abundance of deuterium (0.015%), preferably >30%, more preferably >50%, more preferably >75%, or >95%, or >99%.

In one embodiment, except for H, all or almost all (>99 wt %) of the elements (such as N, C, O, F, etc.) in the compound of formula (I) are naturally existing elements with highest abundance, such as $^{14}$N, $^{12}$C, $^{16}$O and $^{19}$F.

In one embodiment, compounds of formula (I) contain at least one deuterium atom, preferably three deuterium atoms, and more preferably five deuterium atoms.

In one embodiment, R$^1$ is halogen, and preferably chlorine.

In one embodiment, R$^2$ is trifluoromethyl.

In one embodiment, R$^6$ or R$^7$ is independently selected from hydrogen, deuterium, deuterated methyl, or deuterated ethyl; preferably, mono-deuterated methyl, bi-deuterated methyl, tri-deuterated methyl, mono-deuterated ethyl, bi-deuterated ethyl, tri-deuterated ethyl, tetra-deuterated ethyl, or penta-deuterated ethyl.

In one embodiment, R$^6$ or R$^7$ is independently selected from hydrogen, methyl or tri-deuterated methyl.

In one embodiment, R$^3$, R$^4$ or R$^5$ is independently selected from hydrogen or deuterium.

In one embodiment, R$^8$, R$^9$, R$^{10}$ or R$^{11}$ is independently selected from hydrogen or deuterium.

In one embodiment, R$^{12}$, R$^{13}$ or R$^{14}$ is independently selected from hydrogen or deuterium.

In one embodiment, said compound is the preferred compound selected from the group consisting of the following compounds:

N-(4-chloro-3-(trifluoromethyl)phenyl)-N'-(4-(2-(N-(methyl-d$_3$)aminoformyl)-4-pyridyloxy)phenyl)urea (or 4-(4-(3-(4-chloro-3-(trifluoromethyl)phenyl]ureido)-phenoxy)-N-(methyl-d$_3$)picolinamide);

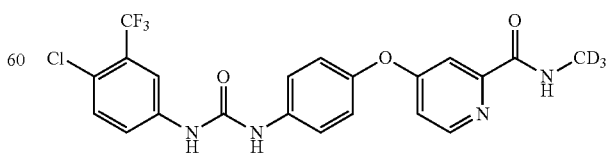

4-(4-(3-(4-chloro-3-(trifluoromethyl)phenyl)ureido)-phenoxy)-2-(N-(methyl-d$_3$)amino formyl)pyridine-1-oxide;

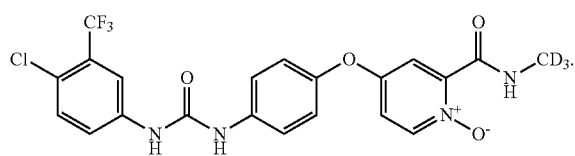 [SMILES: [2H]C([2H])([2H])NC(=O)c1cc(Oc2ccc(NC(=O)Nc3ccc(Cl)c(C(F)(F)F)c3)cc2)cc[n+]1[O-]]

Intermediates

As used herein, the term "the intermediate of the invention" is the compound of formula B:

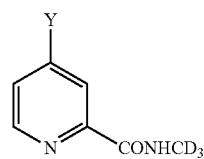

wherein, Y is halogen or

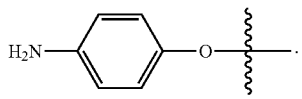

In one embodiment, except for H, all or almost all (>99 wt %) of the elements (such as N, C, O, etc.) in the above compounds are naturally existing elements with highest abundance, such as $^{14}N$, $^{12}C$, and $^{16}O$.

Active Ingredients

As used herein, the term "compound of the invention" refers to the compound of formula (I). This term also includes various crystal forms, pharmaceutically acceptable salts, hydrates or solvates of the compound of formula (I).

As used herein, the term "pharmaceutically acceptable salts" refers to the salts which are suitable for medicine and formed by the compound of the invention and an acid or base. Pharmaceutically acceptable salts include inorganic salts and organic salts. A preferred salt is formed by the compound of the invention and an acid. The acid suitable for forming salts includes, but not limited to, inorganic acid, such as hydrochloric acid, hydrobromic acid, hydrofluoric acid, sulfuric acid, nitric acid, phosphoric acid; organic acid, such as formic acid, acetic acid, propionic acid, oxalic acid, malonic acid, succinic acid, fumaric acid, maleic acid, lactic acid, malic acid, tartaric acid, citric acid, picric acid, methanesulfonic acid, benzene methanesulfonic acid, benzene sulfonic acid; and acidic amino acid, such as aspartic acid, glutamic acid.

Preparation

The preparation methods of compound (I) and the intermediate of formula B are described in detail as below. However, these specific methods are not provided for the limitation of the invention. The compounds of the invention can be readily prepared by optionally combining any of the various methods described in the specification or various methods known in the art, and such combination can readily be carried out by the skilled in the art.

The method for preparing un-deuterated ω-diphenylurea and the physiologically compatible salts thereof used in the invention is known. The deuterated ω-diphenylurea can be prepared in the same route using the corresponding deuterated compounds as starting materials. For example, compound (I) can be prepared according to the method described in WO2000/042012, except that the deuterated material is used instead of un-deuterated material in the reaction.

In general, during the preparation, each reaction is conducted in an inert solvent, at a temperature between room temperature to reflux temperature (such as 0-80° C., preferably 0-50° C.). Generally, the reaction time is 0.1-60 hours, preferably, 0.5-48 hours.

Taking CM4307 as an example, an optimized preparation route is shown as follows:

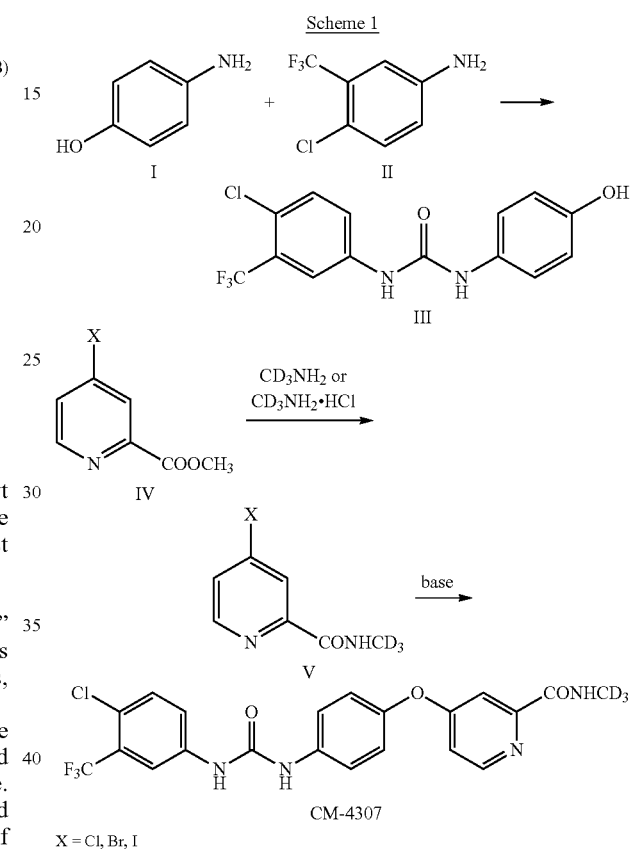

As shown in Scheme 1, in the presence of N,N'-carbonyl-diimidazole, phosgene or triphosgene, 4-aminophenol (Compound I) reacts with 3-trifluoromethyl-4-chloro-aniline (Compound II) to give 1-(4-chloro-3-(trifluromethyl)phenyl)-3-(4-hydroxyphenyl)urea (Compound III). 2-(N-(methyl-d3)) carbamoyl pyridine (Compound V) is obtained by reacting methyl picolinate (Compound IV) with (methyl-d$_3$) amine or (methyl-d$_3$)amine hydrochloride directly or in the presence of the base such as sodium carbonate, potassium carbonate, sodium hydroxide, triethylamine, pyridine and the like. In the presence of base (such as potassium tert-butoxide, sodium hydride, potassium hydride, potassium carbonate, cesium carbonate, potassium phosphate, potassium hydroxide, sodium hydroxide) and an optional catalyst (such as cuprous iodide and proline, or cuprous iodide and picolinic acid), Compound III reacts with Compound V to form compound CM-4307. The above reactions are conducted in an inert solvent, such as dichloromethane, dichloroethane, acetonitrile, n-hexane, toluene, tetrahydrofuran, N,N-dimethylformamide, dimethyl sulfoxide and so on, and at a temperature of 0-200° C.

Taking CM4307 as an example, another preferred process is shown as below:

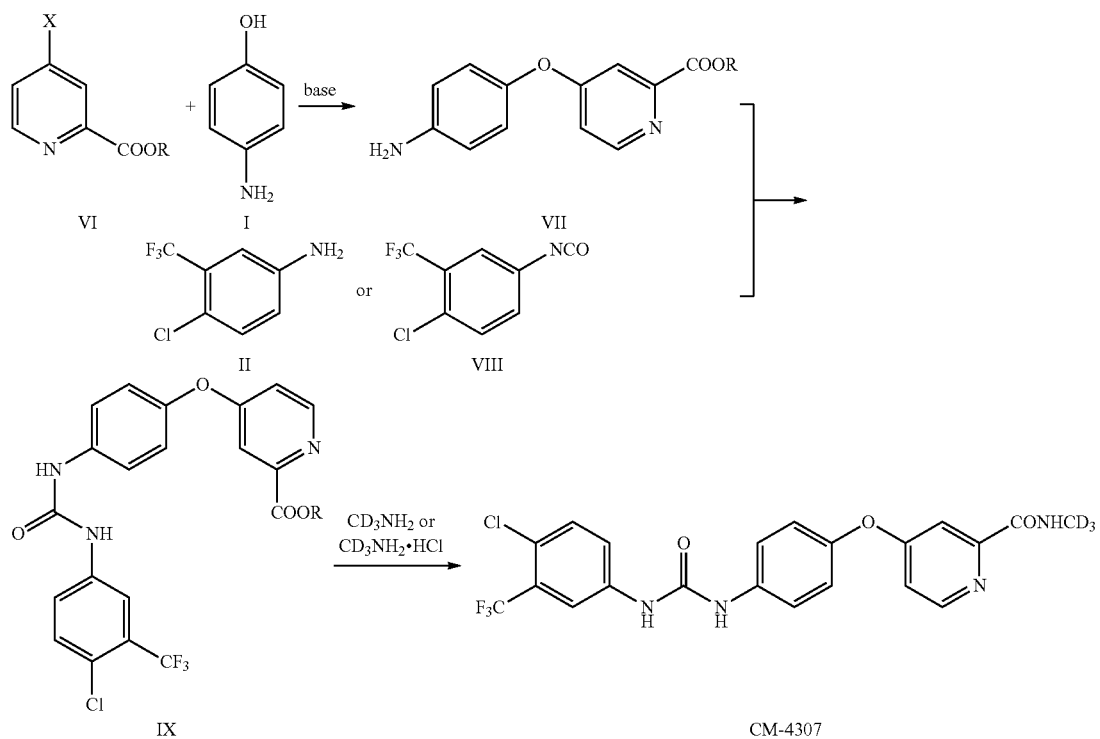

X = Cl, Br, I
R = straight-chain or branched chain C1-C8 alkyl, or aryl

As shown in Scheme 2, amine (Compound VII) is obtained by reacting picolinate (Compound VI) with 4-aminophenol (Compound I) in the presence of base (such as potassium tert-butoxide, sodium hydride, potassium hydride, potassium carbonate, cesium carbonate, potassium phosphate, potassium hydroxide, sodium hydroxide) and an optional catalyst (such as cuprous iodide and proline, or cuprous iodide and pyridine carboxylic acid). The urea (Compound IX) is obtained by reacting Compound VII with Compound II in the presence of N,N'-carbonyldiimidazole, phosgene or triphosgene, or with 1-chloro-4-isocyanato-2-(trifluoromethyl)benzene (Compound VIII). Compound CM4307 is obtained by reacting Compound IX with (methyl-$d_3$)amine or (methyl-$d_3$) amine hydrochloride directly, or in the presence of base (such as sodium carbonate, potassium carbonate, sodium hydroxide, triethylamine, pyridine and the like). The above reactions are conducted in an inert solvent, such as dichloromethane, dichloroethane, acetonitrile, n-hexane, toluene, tetrahydrofuran, N,N-dimethylformamide, dimethyl sulfoxide and so on, and at a temperature of 0-200° C.

Taking CM4307 as an example, another preferred process is shown as below:

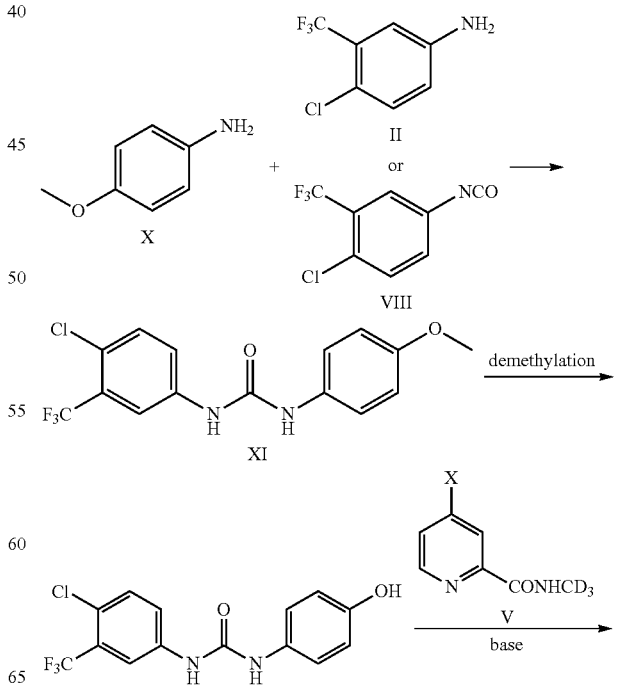

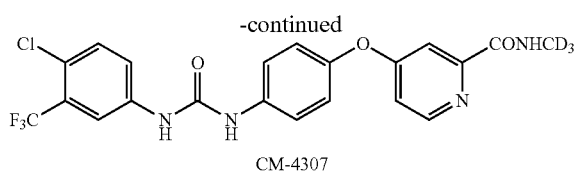

CM-4307

X = Cl, Br, I

As shown in Scheme 3, the urea (Compound XI) is obtained by reacting 4-methyloxyphenylamine (Compound X) with Compound II in the presence of N,N'-carbonyldiimidazole, phosgene or triphosgene, or with 1-chloro-4-isocyanato-2-(trifluoromethyl)benzene (Compound VIII). 1-(4-chloro-3-(trifluromethyl)phenyl)-3-(4-hydroxyphenyl)urea (Compound III) is obtained using any of demethylation methods known in the art. Compound CM4307 is obtained by reacting Compound III with Compound V by the same method as described in Scheme 1, or any methods known in the art. The above reactions are conducted in an insert solvent, such as dichloromethane, dichloroethane, acetonitrile, n-hexane, toluene, tetrahydrofuran, N,N-dimethylformamide, dimethyl sulfoxide and so on, and at a temperature of 0-200° C.

Taking CM4307 as an example, another particularly preferred process is shown as below:

can be repeated to produce high purity deuterated nitromethane. Deuterated nitromethane is reduced in the presence of zinc powder, magnesium powder, iron, or nickel and the like to form deuterated methylamine or the hydrochloride thereof.

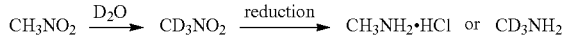

Furthermore, deuterated methylamine or the hydrochloride thereof can be obtained through the following reactions.

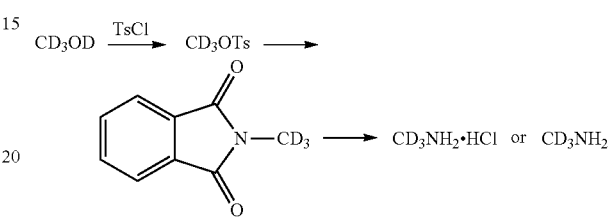

The key intermediate 3 can be synthesized from deuterated methanol (CD$_3$OD) through the following reactions.

Scheme 4

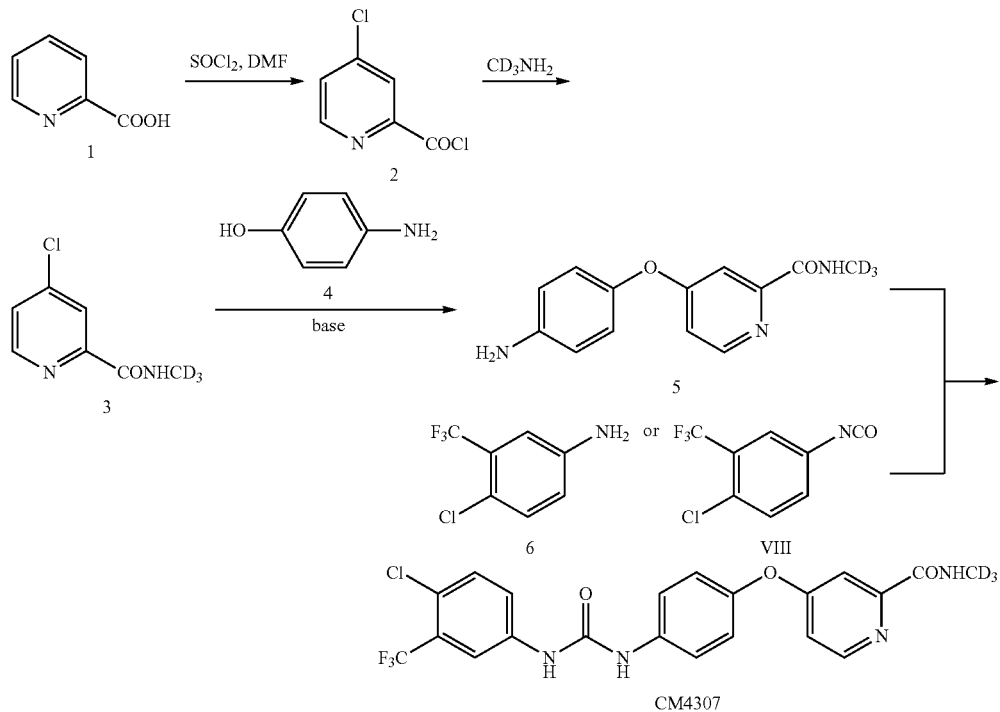

The deuterium can be introduced by using deuterated methylamine.

Deuterated methylamine or the hydrochloride thereof can be prepared through the following reactions. Deuterated nitromethane is obtained by reacting nitromethane with deuterium water in the presence of base (such as sodium hydride, potassium hydride, deuterated sodium hydroxide, deuterated potassium hydroxide, potassium carbonate and the like) or phase-transfer catalyst. If necessary, the above experiment

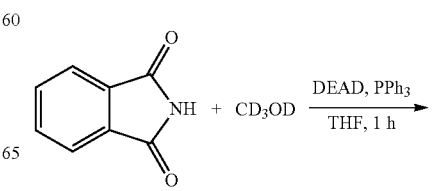

-continued

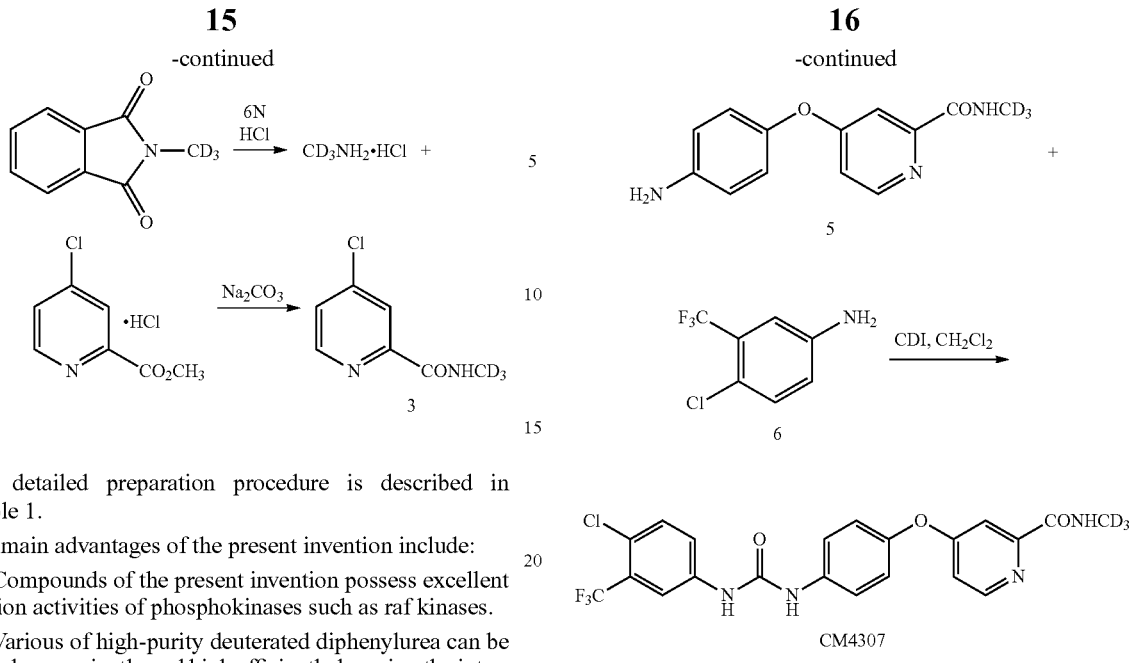

The detailed preparation procedure is described in Example 1.

The main advantages of the present invention include:

(1) Compounds of the present invention possess excellent inhibition activities of phosphokinases such as raf kinases.

(2) Various of high-purity deuterated diphenylurea can be prepared conveniently and high efficiently by using the intermediate of formula B of the invention.

(3) The reaction conditions are milder and the operation is safer.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

EXAMPLE 1

Preparation of N-(4-chloro-3-(trifluoromethyl)phenyl)-N'-(4-(2-(N-(methyl-d$_3$)aminoformyl)-4-pyridyloxy)phenyl)urea (Compound CM4307)

Synthetic Route:

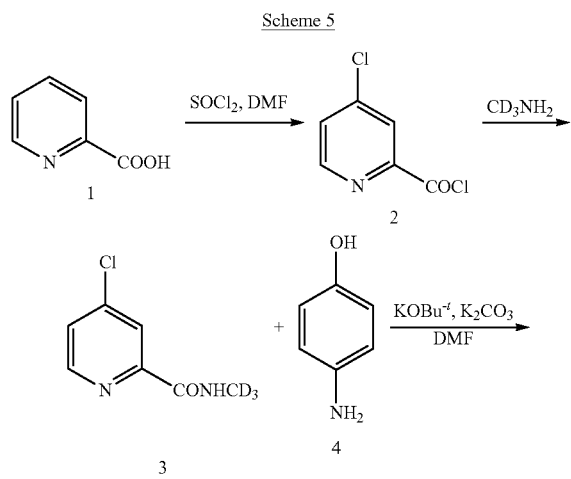

1. Preparation of 4-chloro-N-(methyl-d$_3$)picolinamide (3)

Into a 250 mL single-neck round-bottom flask equipped with waste gas treatment device, thionyl chloride (60 mL) was added. Anhydrous DMF (2 mL) was added slowly dropwise while keeping the temperature at 40-50° C. After addition, the mixture was stirred for 10 min, and then nicotinic acid (20 g, 162.6 mmol) was added in portions over a period of 20 min. The color of the solution gradually changed from green into light purple. The reaction mixture was heated to 70° C., and refluxed for 16 hours with agitation. A great amount of solid precipitate formed. The mixture was cooled to room temperature, diluted with toluene (100 mL) and concentrated to almost dry. The residue was diluted with toluene and concentrated to dry. The residue was filtered and washed with toluene to give 4-chloropicolinoyl chloride as a light yellow solid. The solid was slowly added into a saturated solution of (methyl-d$_3$)amine in tetrahydrofuran in an ice-bath. The mixture was kept below 5° C. and stirred for 5 hours. Then, the mixture was concentrated and ethyl acetate was added to give a white solid precipitate. The mixture was filtered, and the filtrate was washed with saturated brine, dried over sodium sulfate and concentrated to give 4-chloro-N-(methyl-d$_3$)picolinamide (3) (20.68 g, 73% yield) as a light yellow solid.

$^1$H NMR (CDCl$_3$, 300 MHz): 8.37 (d, 1H), 8.13 (s, 1H), 7.96 (br, 1H), 7.37 (d, 1H).

2. Preparation of 4-(4-aminophenoxy)-N-(methyl-d$_3$)picolinamide (5)

To dry DMF (100 mL) 4-aminophenol (9.54 g, 0.087 mol) and potassium tert-butoxide (10.3 g, 0.092 mol) were added in turn. The color of the solution turned into deep brown. After stirring at room temperature for 2 hours, to the reaction mixture was added 4-chloro-N-(methyl-d₃)picolinamide (3) (13.68 g, 0.079 mol) and anhydrous potassium carbonate (6.5 g, 0.0467 mol), then warmed up to 80° C. and stirred over night. TLC detection showed the reaction was complete. The reaction mixture was cooled to room temperature, and poured into a solution mixture of ethyl acetate (150 mL) and saturated brine (150 mL). The mixture was stirred and then stood for layers separation. The aqueous phase was extracted with ethyl acetate (3×100 mL). The extracted layers were combined, washed with saturated brine (3×100 mL) prior to drying over anhydrous sodium sulfate, and concentrated to afford 4-(4-aminophenoxy)-N-(methyl-d₃)picolinamide (18.00 g, 92% yield) as a light yellow solid.

¹H NMR (CDCl₃, 300 MHz): 8.32 (d, 1H), 7.99 (br, 1H), 7.66 (s, 1H), 6.91-6.85 (m, 3H), 6.69 (m, 2H), 3.70 (br, s, 2H).

3. Preparation of N-(4-chloro-3-(trifluoromethyl)phenyl)-N'-(4-(2-(N-(methyl-d₃)aminoformyl)-4-pyridyloxy)phenyl)urea (CM4307)

To methylene chloride (120 mL) was added 4-chloro-3-trifluoromethyl-phenylamine (15.39 g, 78.69 mmol) and N,N'-carbonyldiimidazole (13.55 g, 83.6 mmol). After stirring at room temperature for 16 hours, a solution of 4-(4-aminophenoxy)-N-(methyl-d₃)picolinamide (18 g, 73 mmol) in methylene chloride (180 mL) was slowly added dropwise and the mixture was stirred at room temperature for another 18 hours. TLC detection showed the reaction was complete. The mixture was concentrated to about 100 mL by removing part of methylene chloride through a rotary evaporator and stood for several hours at room temperature. A great amount of white solid precipitated. The solid was filtered and the solid was washed with abundant methylene chloride. The filtrate was concentrated by removing some solvents, and some solids precipitated again. Two parts of solid were combined and washed with abundant methylene chloride to afford N-(4-chloro-3-(trifluoromethyl)phenyl)-N'-(4-(2-(N-(methyl-d₃)aminoformyl)-4-pyridyl oxy)phenyl)urea (CM4307, 20.04 g, 58% yield) as a white powder (pure product).

¹H NMR (CD₃OD, 300 MHz): 8.48 (d, 1H), 8.00 (d, 1H), 7.55 (m, 5H), 7.12 (d, 1H), 7.08 (s, 2H), ESI-HRMS m/z: $C_{21}H_{13}D_3ClF_3N_4O_3$, Calcd. 467.11, Found 490.07 (M+Na)⁺.

Furthermore, Compound CM4307 was dissolved in methylene chloride and reacted with peroxybenzoic acid to afford the corresponding oxidized derivative: 4-(4-(3-(4-chloro-3-(trifluoromethyl)phenyl)ureido)phenoxy)-2-(N-(methyl-d₃)aminoformyl)pyridine-1-oxide.

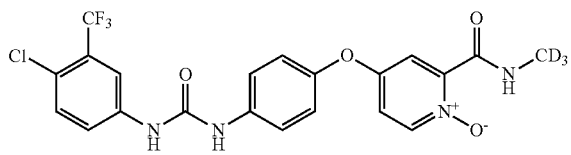 [SMILES: [2H]C([2H])([2H])NC(=O)c1cc(Oc2ccc(NC(=O)Nc3ccc(Cl)c(C(F)(F)F)c3)cc2)cc[n+]1[O-]]

EXAMPLE 2

Preparation of 4-chloro-N-(methyl-d₃)picolinamide (3)

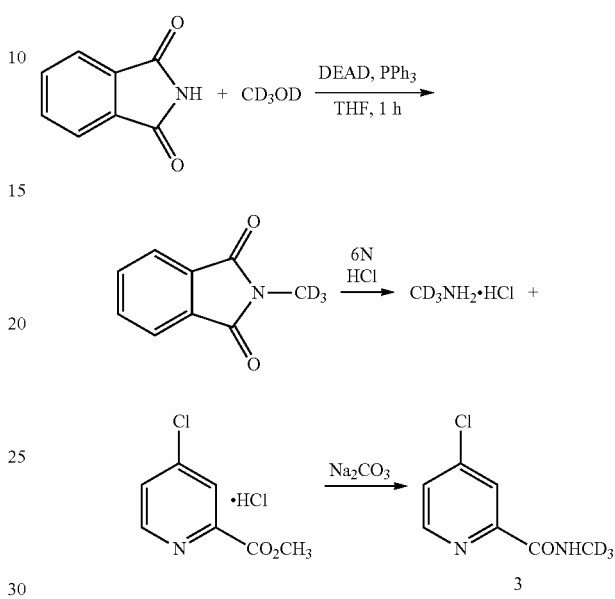

a) Into a solution of phthalimide (14.7 g, 0.1 mol), deuterated methanol (3.78 g, 0.105 mol, 1.05 eq) and triphenylphosphine (28.8 g, 0.11 mol, 1.1 eq) in anhydrous tetrahydrofuran was dropwise added a solution of DEAD (1.1 eq) in tetrahydrofuran under the ice-bath. After addition, the mixture was stirred for 1 hour at room temperature. The mixture was purified by chromatography column, or the solvent in the mixture was removed, and then the residue was dissolved with an appropriate amount of DCM and cooled in the refrigerator to precipitate the solid. The mixture was filtered and the filtrate was concentrated by a rotary evaporator, and then the residue was purified by flash chromatography column to afford the pure product of 2-(N-(methyl-d₃))-isoindole-1,3-dione (14.8 g, 90% yield).

b) 2-(N-(methyl-d₃))-isoindole-1,3-dione (12.5 g, 0.077 mol) was dissolved in hydrochloric acid (6 N, 50 mL) and the mixture was refluxed for 24-30 hours in a sealed tube. The reaction mixture was cooled to room temperature and then cooled below 0° C. in a refrigerator to precipitate the solid. The solid was filtered and washed with cold deionized water. The filtrate was collected and concentrated by a rotary evaporator to remove water and dried to afford (methyl-d₃)amine hydrochloride salt. Anhydrous DCM (100 mL) was added to (methyl-d₃)amine hydrochloride salt and methyl 4-chloropicolinate hydrochloride (6.52 g, 0.038 mol, 0.5 eq) and sodium carbonate (12.2 g, 0.12 mol, 1.5 eq) were added. The reaction flask was sealed and placed in a refrigerator for one day. After TLC detection showed the reaction was complete, the reaction mixture was washed with water, dried, concentrated and purified by chromatography column to afford 4-chloro-N-(methyl-d₃)picolinamide (compound (3), 5.67 g, 86% yield). The structural feature was the same as that in Example 1.

EXAMPLE 3

Preparation of Compound CM4307

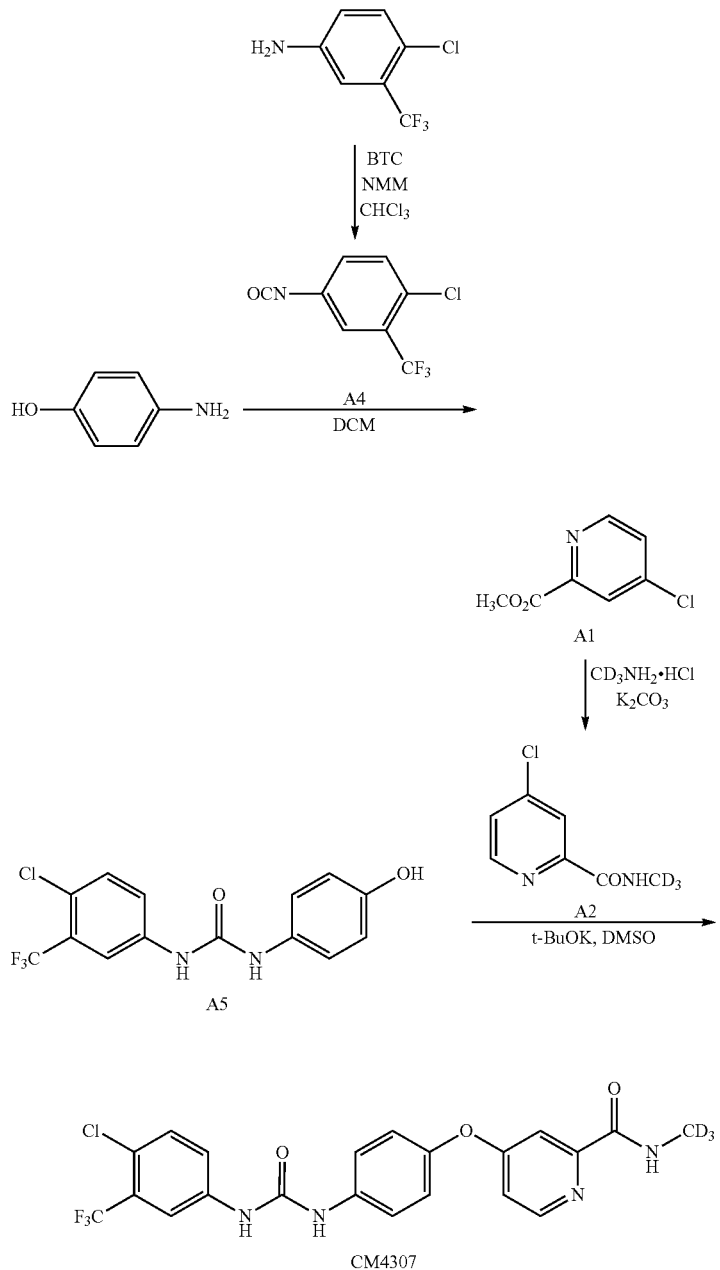

1. Preparation of 1-chloro-4-isocyanato-2-(trifluoromethyl)benzene A4

With a waste gas absorption device, triphosgen (167 g, 0.56 mol, 0.5 eq) was dissolved in chloroform (500 mL). A solution of N-methyl morpholine (11.4 g, 0.11 mol, 0.1 eq) in chlorofrom (100 mL) was added dropwise into the above mixture at 5° C. After addition, a solution of 4-chloro-3-(trifluoromethyl)aniline (220 g, 1.13 mol, 1.0 eq) in chloroform (700 mL) was added dropwise at 10° C. The mixture was warmed to 40° C. and stirred for 15 hours, and then warmed to 50° C. and stirred for 5 hours, and then heated to 60-65° C. and refluxed for 5 hours. The solvent was removed under atmospheric pressure. The residue was distilled under vacumm (oil temperature 110-120° C., vacuum 200 Pa) and the fractions at 95-100° C. were collected to give the title compound (200 g, purity 98.7%, yield 84%) as a colorless liquid.

2: preparation of 4-chloro-N-(methyl-d$_3$)picolinamide (Intermediate A2)

Method 1

To a three-necked flask with tetrahydrofuran (250 mL) was added methyl 4-chloropicolinate (50 g, 0.29 mol, 1 eq), (methyl-d₃)amine hydrochloride (31 g, 0.44 mol, 1.5 eq) and anhydrous potassium carbonate (400-mesh, 80 g, 0.58 mol, 2 eq) with agitation. After the mixture was stirred for 20 hours at room temperature, water (250 mL) and methyl tert-butyl ether (150 mL) were added. After stirring, the organic layer was separated. The aqueous layer was extracted with methyl tert-butyl ether (100 mL). The organic layers were combined, dried over anhydrous sodium sulfate and filtered. The solvent in the filtrate was removed under reduced pressure to give the title compound (48 g, purity 99%, yield 96%) as a light yellow liquid.

$^1$H NMR (DMSO-d₆, 400 MHz): δ7.64 (dd, J=2 Hz, 5.2 Hz, 1H), 7.97 (d, J=1.6 Hz, 1H), 8.54 (d, J=5.2 Hz, 1H), 8.74 (br, 1H).

MS (ESI, m/z) calcd. for C₇H₄D₃ClN₂O: 173, found: 174 [M+H]⁺

Method 2

Methyl 4-chloropicolinate (130 g, 0.76 mol, 1 eq) was dissolved in anhydrous ethanol (1.3 L). (Methyl-d₃)amine hydrochloride (80 g, 1.13 mol, 1.5 eq) and anhydrous potassium carbonate (313 g, 2.67 mol, 3 eq) were added into the mixture with agitation. The mixture was stirred at room temperature for 50 hours. The mixture was filtered and washed with ethanol (260 mL×2), the solvent in the filtrate was removed under reduced pressure, ethyl acetate (400 mL) was added and the resulted mixture was washed with saturated brine (250 mL×2). The aqueous layer was extracted with ethyl acetate (100 mL×2). The organic phases were combined, dried over anhydrous sodium sulfate, and filtered. The solvent in the filtrate was removed under the reduced pressure to give the title compound (109 g, purity 98%, yield 83%) as a light yellow liquid.

$^1$H NMR (DMSO-d₆, 400 MHz): δ7.64 (dd, J=2 Hz, 5.2 Hz, 1H), 7.97 (d, J=1.6 Hz, 1H), 8.54 (d, J=5.2 Hz, 1H), 8.74 (br, 1H).

MS (ESI, m/z) calcd. for C₇H₄D₃ClN₂O: 173, found: 174 [M+H]⁺

3. Preparation of 1-(4-chloro-3-trifluoromethylphenyl)-3-(4-hydroxyphenyl) urea A5

Method 1

4-amino-phenol (5 g, 45.82 mmol, 1 eq) was dissolved in dichloromethane (40 mL) at room temperature. A solution of 1-chloro-4-isocyanato-2-(trifluoromethyl)benzene (10.7 g, 48.11 mmol, 1.05 eq) in dicloromethane (40 mL) was added dropwise. The mixture was stirred at room temperature for 16 hours. The mixture was filtered and washed with dichloromethane (10 mL×2) to give the title compound (14.2 g, purity 97%, yield 94%) as a light brown solid.

$^1$H NMR (DMSO-d₆, 400 MHz): δ6.70 (dd, J=2 Hz, 6.8 Hz, 1H), 7.22 (dd, J=2 Hz, 6.4 Hz, 1H), 7.58-7.24 (m, 1H), 8.10 (d, J=2 Hz, 1H), 8.50 (br, 1H), 9.04 (br, 1H), 9.14 (br, 1H).

MS (ESI, m/z) calcd. for C₁₄H₁₀ClF₂N₂O₃: 330, found: 331 [M+H]⁺

Method 2

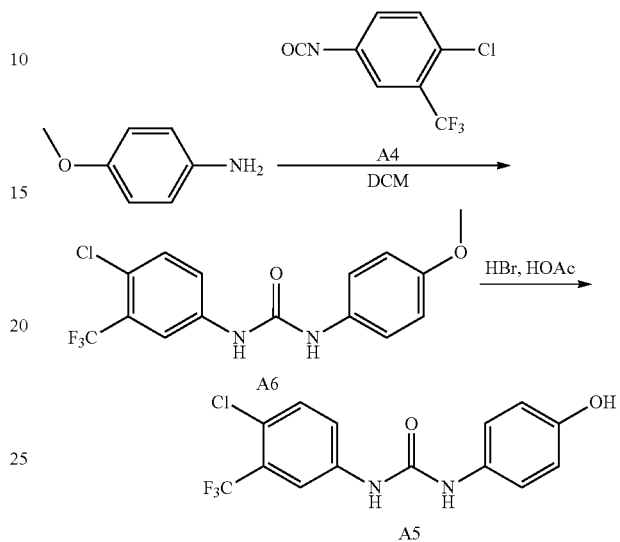

1-chloro-4-isocyanato-2-(trifluoromethyl)benzene (5.15 g, 26 mmol, 1.05 eq) was dissolved in dichloromethane (30 mL). A solution of p-methoxyaniline (3.07 g, 25 mmol, 1 eq) in dichloromethane (20 mL) was added dropwise and the mixture was stirred at room temperature for 20 hours. The mixture was filtered and washed with dichloromethane (5 mL×2). The solid was dissolved in ethyl acetate (50 mL), and the resulted solution was washed with diluted hydrochloric acid (1 N, 10 mL) and saturated brine (20 mL). The organic phase was dried over anhydrous sodium sulfate and the solvent was removed under reduced pressure to give 1-(4-chloro-3-trifluoromethylphenyl)-3-(4-methoxyphenyl)urea A6 (4.5 g, yield 52%) as a white solid.

$^1$H NMR (DMSO-d₆, 400 MHz): δ3.73 (s, 3H), 6.86-6.90 (m, 2H), 7.35-7.39 (m, 2H), 7.59-7.65 (m, 2H), 8.11 (d, J=2 Hz, 1H), 8.65 (br, 1H), 9.09 (br, 1H).

MS (ESI, m/z) calcd. for C₁₅H₁₂ClF₃N₂O₂: 344, found: 345 [M+H]⁺.

1-(4-chloro-3-trifluoromethylphenyl)-3-(4-methoxyphenyl)urea A6 (344 mg, 1 mmol, 1 eq) was dissolved in acetic acid (4 mL). Hydrobromic acid (40%, 1 mL) was added and the mixture was refluxed for 5 hours. The mixture was cooled to room temperature and ice water (10 mL) was added. The mixture was extracted with ethyl acetate (20 mL). The organic phase was washed with saturated sodium bicarbonate (10 mL), dried over anhydrous sodium sulfate. The solvent in the organic phase was removed under reduced pressure to give the title compound (140 mg, purity 90%, yield 42%) as a light yellow solid.

$^1$H NMR (DMSO-d₆, 400 MHz): δ6.70 (dd, J=2 Hz, 6.8 Hz, 1H), 7.22 (dd, J=2 Hz, 6.4 Hz, 1H), 7.58-7.24 (m, 1H), 8.10 (d, J=2 Hz, 1H), 8.50 (br, 1H), 9.04 (br, 1H), 9.14 (br, 1H).

MS (ESI, m/z) calcd. for C₁₄H₁₀ClF₃N₂O₂: 330, found: 331 [M+H]⁺

4. Preparation of 4-(4-(3-(4-chloro-3-(trifluoromethyl)phenyl]ureido)-phenoxy)-N-(methyl-d₃)picolinamide (CM4307)

1-(4-chloro-3-trifluoromethyl-phenyl)-3-(4-hydroxy-phenyl)urea A5 (4 g, 12.10 mmol, 1 eq) was dissolved in N,N-dimethyl formamide (20 mL). Potassium tert-butoxide (4.6 g, 41.13 mmol, 3.4 eq) was added in portions. After the mixture was stirred for 3 hours, 4-chloro-N-(methyl-d₃)picolinamide (2.3 g, 13.31 mmol, 1.1 eq) and potassium carbonate (0.8 g, 6.05 mmol, 0.5 eq) was added. The mixture was heated to 80° C. and stirred for 1.5 hours. The mixture was cooled to room temperature and ethyl acetate (200 mL) was added, and filtered to remove the inorganic salts. The filtrate was washed with saturated brine (50 mL×3) and the organic layer was separated. The organic phase was dried over anhydrous sodium sulfate and filtered. The solvent was removed under reduced pressure to give a solid followed by adding acetonitrile (15 mL). The resulted mixture was refluxed for 2 hours, cooled to room temperature, and filtered to give CM4307 (3.4 g, purity 96%, yield 60%) as a light yellow solid.

$^1$H NMR (DMSO-d₆, 400 MHz): δ7.15 (dd, J=2.8 Hz, 5.6 Hz, 1H), 7.17-7.19 (m, 2H), 7.40 (d, J=2.4 Hz, 1H), 7.59-7.69 (m, 4H), 8.13 (d, J=2.4 Hz, 1H), 8.51 (d, J=6 Hz, 1H), 8.75 (br, 1H), 8.90 (br, 1H), 9.22 (br, 1H).

MS (ESI, m/z) calcd. for $C_{21}H_{13}D_3ClF_3N_4O_3$: 467, found: 468 [M+H]$^+$.

EXAMPLE 4

Preparation of Compound CM4307

1. Preparation of 4-chloro-N-(methyl-d₃)picolinamide (Intermediate A2)

Under nitrogen, tetrahydronfuran (10.86 kg) was added into a reactor (30 L). After the mixer was started, (N-(methyl-d₃))amine hydrochloride (1.50 kg, 21.26 mol, 1.5 eq), methyl 4-chloropicolinate (2.43 kg, 14.16 mol, 1 eq) and anhydrous potassium carbonate (3.92 kg, 28.36 mol, 2 eq) were added in turn. The reaction was conducted at 33° C. for 15 h, and then pure water (12.20 kg) was added. The reaction mixture was extracted with methyl tert-butyl ether (3.70 kg×2). The organic phases were combined, dried over anhydrous sodium sulfate (0.50 kg) and stirred for 1 hour, and filtered. The solvents were removed under vacuum (≤0.09 MPa) at 40±2° C. with water bath to give the title compound (2.41 kg, purity 99.0%, yield 98%) as a light yellow oil.

$^1$H NMR (DMSO-d₆, 400 MHz): δ7.64 (dd, J=2 Hz, 5.2 Hz, 1H), 7.97 (d, J=1.6 Hz, 1H), 8.54 (d, J=5.2 Hz, 1H), 8.74 (br, 1H).

MS (ESL m/z) calcd. for $C_7H_4D_3ClN_2O$: 173, found: 174 [M+H]$^+$

2. Preparation of 4-(4-aminophenoxy)-N-(methyl-d₃) picolinamide (Intermediate A3)

Method 1

Under nitrogen, dimethylsulfoxide (2.75 kg) was added into a reactor (20 L). After the mixer was started, 4-chloro-N-(methyl-d₃)picolinamide (2.41 kg, 13.88 mol, 1 eq),

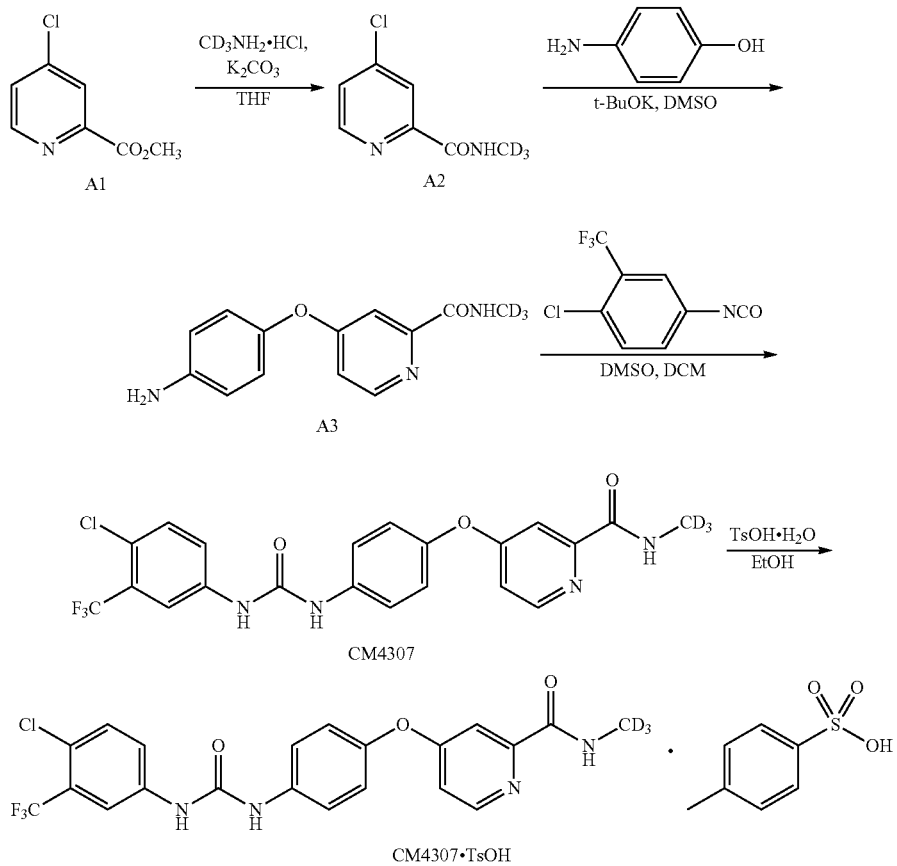

4-aminophenyol (1.62 kg, 14.84 mol, 1.08 eq) and potassium tert-butoxide (1.66 kg, 14.79 mol, 1.1 eq) were added in turn. After the temperature of the reactor was stable, the inner temperature was heated to 80° C. and stirred for 4 hours. After the inner temperature was cooled to 40° C., isopropanol (7.90 kg) was added to dilute the reaction mixture with stirring. The reactor was washed by isopropanol, and the resulted mixture was transferred to a reactor (30 L). Under nitrogen, hydrochloric acid (5.81 kg) was added dropwise. After the addition, the mixture was stirred, filtered by centrifugation, and washed with pure water. The solid was transferred into a reactor (50 L), and completely dissolved in water (21.00 kg) with stirring. Under nitrogen, a solution of potassium carbonate (2.5 kg potassium carbonate dissolved in 7 L pure water) was added dropwise into the above reactor (50 L) for about 1.5 hours. The mixture was discharged and centrifuged, and the product was washed with pure water and driedunder vacuum for 24 hours to give the title compound (2.72 kg, purity 99.9%, yield 78%) as a light brown crystal.

$^1$H NMR (DMSO-$d_6$, 400 MHz): 135.19 (br, 2H), 6.66-6.68 (m, 2H), 6.86-6.88 (m, 2H), 7.07 (dd, J=2.8 Hz, 5.6 Hz, 1H), 7.36 (d, J=2.8 Hz, 1H), 8.45 (d, J=5.6 Hz, 1H), 8.72 (br, 1H).

MS (ESI, m/z) calcd. for $C_{13}H_{10}D_3N_3O_2Cl$: 246, found: 247 [M+H]$^+$.

Method 2

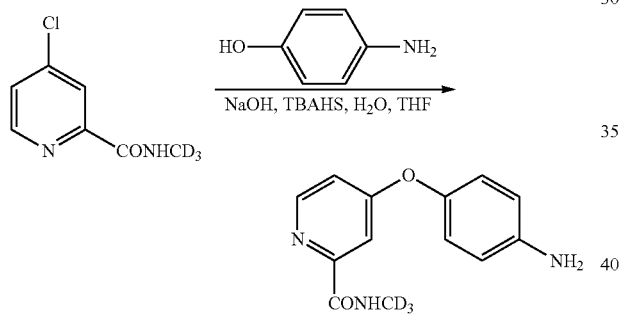

4-chloro-N-(methyl-$d_3$)picolinamide (4.3 g, 24.77 mmol, 1 eq) was dissolved in tetrahydrofuran (20 mL) at room temperature. 4-aminophenol (2.7 g, 24.77 mmol, 1 eq), tetrabutylammonium hydrogen sulfate (1.68 g, 4.95 mmol, 0.2 eq) and sodium hydroxide (1.35 g, 33.69 mmol, 1.36 eq) was added with stirring at room temperature. A solution of sodium hydroxide in water (45%, sodium hydroxide (1.32 g) was dissolved in water (1.6 mL)) was added dropwise slowly. The mixture was heated to 67° C. and stirred for 20 hours. The mixture was cooled to below 20° C., and concentrated hydrochloric acid (37%, 10 mL) was added at a rate keeping the reaction temperature below 25° C. The mixture was stirred for 1 hour, filtered and washed with tetrahydrofuran (20 mL). The resulted solid was dissolved in water (60 mL). The mixture was cooled to 10-20° C. and slowly added dropwise a solution of sodium hydroxide (22.5%, 2.6 mL) till the pH was 3-3.5. A solution of sodium hydroxide (22.5%, 3.4 mL) was continuously added till the pH was 7-8 and a light yellow solid precipitated. During the addition, the temperature of the mixture was kept below 20° C. The mixture was filtered and the solid was washed with water (12 mL×2). The solid was dried under vacuum to give 4-(4-aminophenoxy)-N-(methyl-$d_3$)picolinamide (5.01 g, purity 99%, yield 82%) as a light yellow solid.

$^1$H NMR (DMSO-$d_6$, 400 MHz): δ5.19 (br, 2H), 6.66-6.68 (m, 2H), 6.86-6.88 (m, 2H), 7.07 (dd, J=2.8 Hz, 5.6 Hz, 1H), 7.36 (d, J=2.8 Hz, 1H), 8.45 (d, J=5.6 Hz, 1H), 8.72 (br, 1H).

MS (ESI, m/z) calcd. for $C_{13}H_{10}D_3N_3O_2Cl$: 246, found: 247 [M+H]$^+$

3. Preparation of 4-(4-(3-(4-chloro-3-(trifluoromethyl)phenyl]ureido)-phenoxy)-N-(methyl-$d_3$)picolinamide (CM4307)

Under nitrogen, dichloromethane (17.30 kg) and dimethylsulfoxide (2.92 kg) was added into a dry reactor (50 L). The mixture was stirred at room temperature, 4-(4-aminophenoxy)-N-(methyl-$d_3$)picolinamide (2.65 kg, 10.76 mol) was added. 1-chloro-4-isocyanato-2-(trifluoromethyl)benzene (2.50 kg, 11.26 mol, 1.05 eq) was dissolved in dichloromethane (7.00 kg). The solution of 1-chloro-4-isocyanato-2-(trifluoromethyl)benzene in dichloromethane was dropwise added into the reactor. The reaction was conducted for 10 min at room temperature. The reaction mixture was cooled to 3±2° C. by an ice-brine bath. Pure water (10.60 kg) was dropwise added into the reactor while keeping the temperature at 3±2° C. After the addition, the mixture was stirred for 30 min, then discharged and centrifuged. The product was washed with dichloromethane (7.00 kg). The resulted product was dried under vacuum for 24 h to give an off-white powder (4.8 kg, purity 99.8%, yield 95.4%).

$^1$H NMR (DMSO-$d_6$, 400 MHz): δ7.15 (dd, J=2.8 Hz, 5.6 Hz, 1H), 7.17-7.19 (m, 2H), 7.40 (d, J=2.4 Hz, 1H), 7.59-7.69 (m, 4H), 8.13 (d, J=2.4 Hz, 1H), 8.51 (d, J=6 Hz, 1H), 8.75 (br, 1H), 8.90 (br, 1H), 9.22 (br, 1H).

MS (ESI, m/z) calcd. for $C_{21}H_{13}D_3ClF_3N_4O_3$: 467, found: 468 [M+H]$^+$

EXAMPLE 5

Preparation of 4-(4-(3-(4-chloro-3-(trifluoromethyl)phenyl)ureido)-phenoxy)-N-(methyl-$d_3$)picolinamide p-toluenesulfonate (CM4307•TsOH)

A reactor (100 L) was charged with anhydrous ethanol (45.00 kg). After the mixer was started, 4-(4-(3-(4-chloro-3-(trifluoromethyl)phenyl]ureido)-phenyoxy)-N-(methyl-$d_3$) picolinamide (4.50 kg, 9.62 mol, 1 eq) and p-toluenesulfonic acid monohydrate (0.66 kg, 3.47 mol, 0.36 eq) were added separately. The mixture was heated to 78° C. and refluxed for 40 min till the solid was fully dissolved.

p-toluenesulfonic acid monohydrate (1.61 kg, 8.46 mol) was added into anhydrous ethanol (4.50 kg), and the mixture was heated to 70° C. till the solid was dissolved. The resulted solution was added into the reactor (100 L). The mixture was cooled to 0-2° C. and kept for 30 min. The mixture was discharged and centrifugally filtered. The solid was washed with anhydrous ethanol (13.50 kg), dried under vacuum for 24 h to give the title compound (5.75 kg, purity 99.3%, yield 93.4%) as a white to off-white solid.

$^1$H NMR (DMSO-$d_6$, 400 MHz): δ2.30 (s, 3H), 7.15 (d, J=8.8 Hz, 2H), 7.20 (d, J=8.8 Hz, 2H), 7.23 (dd, J=2.8 Hz, 6 Hz, 1H), 7.52 (d, J=8 Hz, 2H), 7.55 (d, J=2.8 Hz, 1H), 7.63 (d, J=8.8 Hz, 3H), 7.68 (dd, J=2.4 Hz, 9.2 Hz, 1H), 8.03 (br, 1H), 8.14 (d, J=2.4 Hz, 1H), 8.56 (d, J=6 Hz, 1H), 8.91 (br, 1H), 9.17 (br, 1H), 9.36 (br, 1H).

$^{13}$C NMR (DMSO-$d_6$, 400 MHz): δ2.1, 26.1, 111.7, 115.2, 117.0, 120.7 (2C), 121.6 (2C), 121.9, 122.8, 123.2, 124.6, 125.6 (2C), 127.2, 129.0 (2C), 132.3, 138.8, 139.5, 139.9, 144.1, 146.6, 147.2, 152.8, 159.9, 170.7 ppm.

Liquid chromatography condition: Agilent 1100 Series; chromatographic column: Synergi 4μ POLAR-RP 80A, 250× 4.6 mm, 4 μm; column temperature: 25° C.; detection wavelength: UV 210 nm; mobile phase: A: ammonium dihydrogen phosphate 10 mmol/L, B: methanol; injection volume: 10 μL; flow rate: 0.8 mL/min; run time: 70 min; gradient: 50% mobile phase B from 0 to 15 min, mobile phase B being increased to 75% from 15 to 32 min, then 75% mobile phase B eluting for 23 min from 32 to 55 min. retention time: 4.95 min (p-toluenesulfonic acid); 47.11 min (CM4307).

EXAMPLE 6

Preparation of Compound CM4307

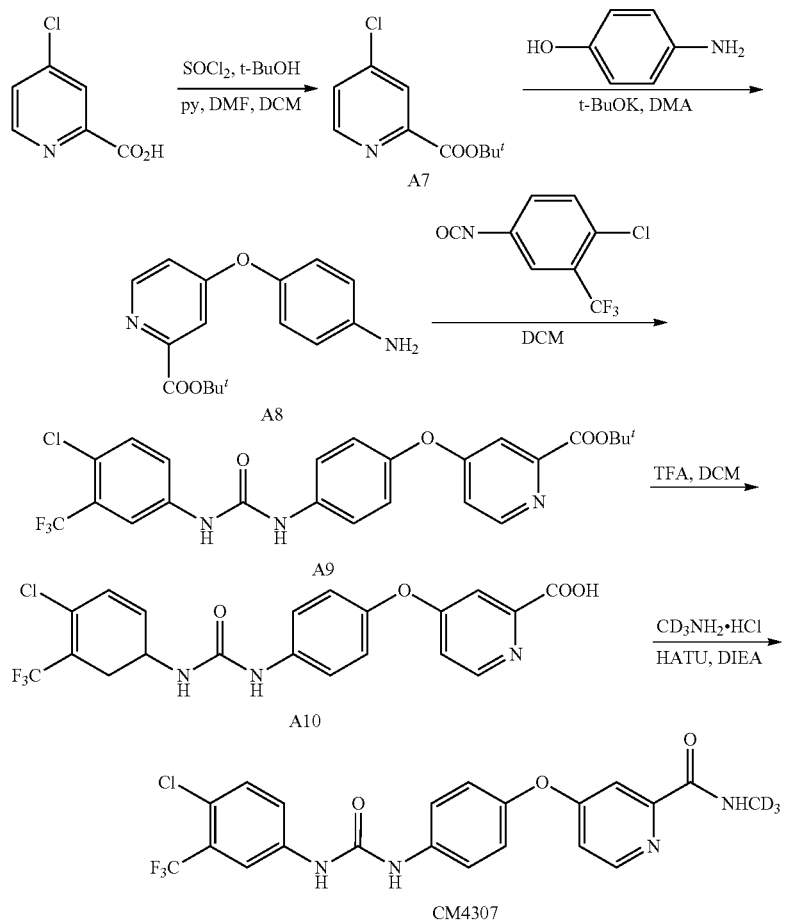

1: Preparation of tert-butyl 4-chloropicolinate A7

4-chloropicolinic acid (10.5 g, 66.64 mmol) was suspended in thionyl chloride (40 mL), and the mixture was heated to 80° C. and refluxed. N,N-dimethylformamide (0.2 mL) was added dropwise, and the mixture was refluxed for 2 hours. The excess of thionyl chloride was removed under reduced pressure to give the pale yellow acyl chloride, followed by addition of dichloromethane (60 mL). The resulted solution was added into a mixed solution of tert-butanol (25 mL), pyridine (20 mL) and dichloromethane (80 mL) at −40° C. The reraction mixture was heated to 50° C. and stirred for 16 hours. The solvents were removed under reduced pressure and ethyl acetate (150 mL) was added. The resulted mixture was washed with saturated brine (50 mL×2) and a sodium hydroxide solution (1 N, 50 mL×2), and separated. The organic phase was dried over anhydrous sodium sulfate and concentrated under the reduced pressure. The residue was dried under vacuum to give the title compound (11.1 g, purity 95%, yield 78%) as a pale yellow solid.

$^1$H NMR (DMSO-$d_6$, 400 MHz): δ1.56 (s, 9H), 7.80 (dd, J=2.4 Hz, 5.2 Hz, 1H), 8.02 (d, J=2 Hz, 1H), 8.69 (d, J=5.2 Hz, 1H).

MS (ESI, m/z) calcd. for $C_{10}H_{12}ClNO_2$: 213, found: 158 [M−Bu$^t$+H]$^+$

2: Preparation of tert-butyl 4-(4-aminophenoxy)picolinate A8

At room temperature, p-aminophenol (0.51 g, 4.70 mmol, 1 eq) was dissolved in N,N-dimethylformamide (10 mL). To the resulted solution, potassium tert-butoxide (0.53 g, 4.70 mmol, 1 eq) was added in portions and the resulted mixture was stirred for 0.5 hours. Tert-butyl 4-chloropicolinate (1 g, 4.70 mmol, 1 eq) and potassium carbonate (45 mg, 0.33 mmol, 0.07 eq) were added, and the mixture was heated to 80° C. and stirred for 2 hours. The mixture was cooled to room temperature and ethyl acetate (50 mL) was added. The mixture was filtered to remove the undissolved material and the filtrate was washed with saturated brine (20 mL×2). The organic phase was dried over anhydrous sodium sulfate, concentrated under reduced pressure to remove the solvent. The residue was purified by column chromatography (dicloromethane:ethyl acetate=30:1) to give the title compound (805 mg, purity 96%, yield 60%).

$^1$H NMR (DMSO-$d_6$, 400 MHz): δ1.52 (s, 9H), 5.21 (br, 2H), 6.64 (d, J=8.8 Hz, 2H), 6.87 (d, J=8 Hz, 2H), 7.35 (dd, J=2.4 Hz, 5.6 Hz, 1H), 8.50 (d, J=6 Hz, 1H).

MS (ESI, m/z) calcd. for $C_{10}H_{12}ClNO_2$: 286, found: 231 $[M-Bu^t+H]^+$

3: Preparation of tert-butyl 4-(4-(3-(4-chloro-3-(trifluoromethyl)phenyl)ureido)phenoxy)picolinate A9

At room temperature, 1-chloro-4-isocyanato-2-(trifluoromethyl)benzene (656 mg, 2.96 mmol, 1.05 eq) was disolved in dichloromethane (5 mL). To the resulted solution, a solution of tert-butyl 4-(4-aminophenoxy)picolinate (805 mg, 2.81 mmol, 1 eq) in dichloromethane (5 mL) was slowly added dropwise. The mixture was stirred for 16 hours at room temperature. The solvent was removed under reduced pressure, and the resulted solid was purified by column chromatography (dichoromethane:methanol=30:1) to give the title compound (1.4 g, putity 95%, yield 85%) as a white solid.

$^1$H NMR (DMSO-$d_6$, 400 MHz): δ1.53 (s, 9H), 7.13 (dd, J=2.4 Hz, 5.2 Hz, 1H), 7.18 (d, J=8.8 Hz, 2H), 7.41 (d, J=2.4 Hz, 1H), 7.59-7.66 (m, 4H), 8.13 (d, J=1.6 Hz, 1H), 8.55 (d, J=5.6 Hz, 1H), 9.06 (br, 1H), 9.27 (br, 1H).

MS (ESI, m/z) calcd. for $C_{24}H_{21}ClF_3N_3O_4$: 507, found: 508 $[M+H]^+$

4: Preparation of 4-(4-(3-(4-chloro-3-(trifluoromethyl)phenyl)ureido) phenoxy)picolinic acid A10

At room temperature, tert-butyl 4-(4-(3-(4-chloro-3-(trifluoromethyl)phenyl) ureido)phenoxy)picolinate (1.4 g, 2.76 mmol) was dissolved in dichloromethane (20 mL). To the resulted solution, trifluoroacetic acid (20 mL) and triethylsilane (0.5 mL) were added. The resulted mixture was heated to 50° C. and stirred for 16 hours. The solvent was removed under reduced pressure, and water (50 mL) and ethyl acetate (70 mL) were added. The resulted mixture was separsted and the organic phase was removed. The aqueous layer was filtered and the solid was washed with water (30 mL×2). The solid was dried under vacumn to give the title compound (1.1 g, purity 97%, yield 90%) as a light green solid.

$^1$H NMR (DMSO-$d_6$, 400 MHz): δ7.21-7.25 (m, 2H), 7.33 (dd, J=2.8 Hz, 6 Hz, 1H), 7.57 (d, J=2.8 Hz, 1H), 7.60-7.67 (m, 4H), 8.12 (d, J=2.4 Hz, 2H), 8.64 (d, J=6 Hz, 1H), 9.84 (br, 1H), 10.17 (br, 1H).

MS (ESI, m/z) calcd. for $C_{20}H_{12}ClF_4N_3O_4$: 451, found: 450 $[M-H]^-$

5: Preparation of 4-(4-(3-(4-chloro-3-(trifluoromethyl)phenyl]ureido)-phenoxy)-N-(methyl-$d_3$)picolinamide CM4307

Method 1

At room temperature, 4-(4-(3-(4-chloro-3-(trifluoromethyl)phenyl)ureido) phenoxy)picolinic acid (0.5 g, 1.11 mmol, 1 eq) was disolved in N,N-dimethylforamide (5 mL). To the resulted solution, (N-(methyl-$d_3$))amine hydrochloride (0.15 g, 2.22 mmol, 2 eq), 2-(7-aza-1H-benzotriazole-1-yl)-N,N,N'N'-tetramethyluronium hexafluorophosphate (HATU, 0.84 g, 2.22 mmol, 2 eq) and N,N-diisopropylethylamine (DIEA, 0.86 g, 6.66 mmol, 3 eq) were added. The resulted mixture was stirred at room temperature for 16 hours. To the above reaction mixture, water (20 mL) was added. The resulted mixture was stirred for 0.5 hour and then filtered to give a pale-white solid. The solid was dissolved in ethyl acetate (50 mL), and the resulted mixture was washed with saturated brine (10 mL×3), and then separated. The organic phase was dried over anhydrous sodium sulfate and filtered. The solvent in the filtrate was removed under reduced pressure to give CM4307 (0.42 g, purity 97%, yield 81%) as an off-white solid.

$^1$H NMR (DMSO-$d_6$, 400 MHz): δ7.15 (dd, J=2.8 Hz, 5.6 Hz, 1H), 7.17-7.19 (m, 2H), 7.40 (d, J=2.4 Hz, 1H), 7.59-7.69 (m, 4H), 8.13 (d, J=2.4 Hz, 1H), 8.51 (d, J=6 Hz, 1H), 8.75 (br, 1H), 8.90 (br, 1H), 9.22 (br, 1H).

MS (ESI, m/z) calcd. for $C_{21}H_{13}D_3ClF_3N_4O_3$: 467, found: 468 $[M+H]^+$ Method 2

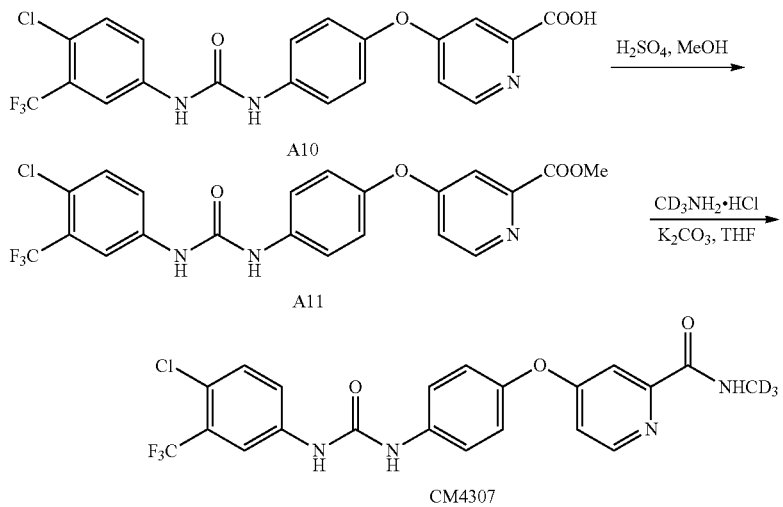

4-(4-(3-(4-chloro-3-(trifluoromethyl)phenyl)ureido)phe-noxy)picolinic acid (0.5 g, 1.11 mmol) was suspended in methanol (10 mL). Concentrated sulfuric acid (2 mL) was added at room temperature, and the resulted mixture was refluxed for 3 hours. The solvent was removed under reduced pressure, and the residue was purified by column chromatography (dichloromethane:methanol=10:1) to give methyl 4-(4-(3-(4-chloro-3-(trifluoromethyl)phenyl)ureido)phenoxy)picolinate A11 (0.46 g, purity 95%, yield 90%) as a white solid.

$^1$H NMR (DMSO-$d_6$, 400 MHz): δ3.85 (s, 3H), 7.18-7.21 (m, 3H), 7.43 (d, (dd, J=2.4 Hz, 1H), 7.59-7.66 (m, 4H), 8.13 (d, J=2.4 Hz, 1H), 8.59 (d, J=6 Hz, 1H), 9.06 (br, 1H), 9.27 (br, 1H).

MS (ESI, m/z) calcd. for $C_{21}H_{15}ClF_3N_3O_4$: 465, found: 466 $[M+H]^+$

Methyl 4-(4-(3-(4-chloro-3-(trifluoromethyl)phenyl)ureido)phenoxy)picolinate (300 mg, 0.65 mmol, 1 eq) was added into a three-necked bottle containing tetrahydrofuran (10 mL) with stirring. To the resulted mixture, (N-(methyl-$d_3$))amine hydrochloride (91 mg, 1.3 mmol, 2 eq) and anhydrous potassium carbonate (400 mesh, 179 mg, 1.3 mmol, 2 eq) were added. After the mixture was stirred at room temperature for 20 hours, water (5 mL) and methyl ter-butyl ether (15 mL) were added. The mixture was stirred and separated the organic phase. The aqueous layer was extracted with methyl ter-butyl ether (10 mL), and the organinc layers were combined, dried over anhydrous soudium sulfate and filtered. The solvent in the filtrate was removed under reduced pressure to afford CM4307 (261 mg, purity 96%, yield 86%) as an off-white solid.

$^1$H NMR (DMSO-$d_6$, 400 MHz): δ7.15 (dd, J=2.8 Hz, 5.6 Hz, 1H), 7.17-7.19 (m, 2H), 7.40 (d, J=2.4 Hz, 1H), 7.59-7.69 (m, 4H), 8.13 (d, J=2.4 Hz, 1H), 8.51 (d, J=6 Hz, 1H), 8.75 (br, 1H), 8.90 (br, 1H), 9.22 (br, 1H).

MS (ESI, m/z) calcd. for $C_{21}H_{13}D_3ClF_3N_4O_3$: 467, found: 468 $[M+H]^+$

EXAMPLE 7

Pharmacokinetic Evaluation for Deuterated Diphenylurea Compounds in Rats 8 male Sprague-Dawley rats, 7-8 weeks-old and body weight about 210 g, were divided into two groups, 4 in each group (rat No.: control group was 13-16; experimental group was 9-12). The rats were orally administrated at a single dose of 3 mg/kg of (a) the undeuterated compound N-(4-chloro-3-(trifluoromethyl)phenyl)-N'-(4-(2-(N-methyl-amino-formyl)-4-pyridyloxy) phenyl)urea (control compound CM4306) or (b) N-(4-chloro-3-(trifluoromethyl)phenyl)-N'-(4-(2-(N-(methyl-$d_3$)-aminoformyl)-4-pyridyloxy)phenyl) urea (Compound CM4307 of the invention) prepared in Example 1. The pharmacokinetics differences of CM4306 and CM4307 were compared.

The rats were fed with the standard feed, given water and chlordiazepoxide. Chlordiazepoxide was stopped at the last night before experiment, and given again two hours after the administration of the compound. The rats were fasted for 16 hours before the test. The compound was dissolved in 30% PEG400. The time for collecting orbital blood was 0.083, 0.25, 0.5, 1, 2, 4, 6, 8 and 24 hours after administration of the compound.

The rats were anaesthetised briefly by inhaling ether. A 300 μL orbital blood sample was collected into the tubes containing a 30 μl 1% heparin saline solution. The tubes were dried overnight at 60° C. before use. After the blood samples were subsequentially collected, the rats were anaesthetised by ether and sacrificed.

After the blood samples were collected, the tubes were gently reversed at least five times immediately to mix the contents sufficiently, and placed on the ice. The blood samples were centrifuged at 4° C. at 5000 rpm for 5 minutes to separate the serum and red blood cells. 100 μL serum was removed to a clean plastic centrifugal tube by pipettor, and the name of the compound and time point was labeled on the tube. Serum was stored at –80° C. before LC-MS analysis.

Figure 2:
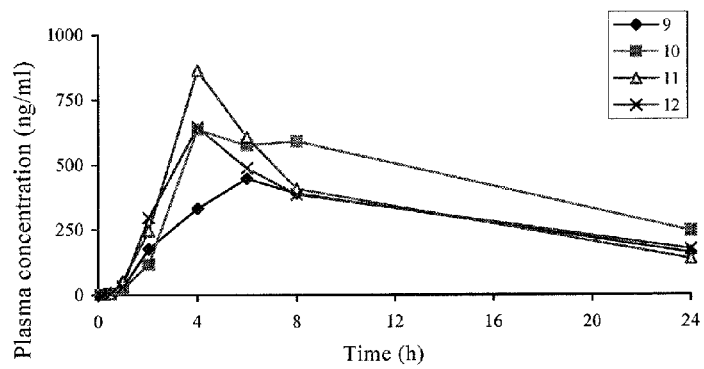
FIG. 2 shows the curves of drug concentration (ng/ml) in plasma after oral administration 3 mg/kg of the compound CM4307 of the invention to the male SD rats.

The results were shown in FIGS. 1-2. The results showed that, compared with CM4306, the half-life ($T_{1/2}$) of CM4307 was longer [11.3±2.1 hours for CM4307 and 8.6±1.4 hours for CM4306, respectively], area under the curve ($AUC_{0-\infty}$) of CM4307 was significantly increased [11255±2472 ng·h/mL for CM4307 and 7328±336 ng·h/mL for CM4306, respectively], and apparent clearance of CM4307 was reduced [275±52 mL/h/kg for CM4307 and 410±18.7 mL/h/kg for CM4306, respectively].

The above results showed that, the compound of the present invention had better pharmacokinetics properties in the animal, and thus had better pharmacodynamics and therapeutic effects.

In addition, the metabolism for the compound of the present invention in organism was changed through deuteration. In particular, the hydroxylation of phenyl became more difficult, which led to the reduction of first-pass effect. In such cases, the dose can be changed, long-acting preparations can be formed, and the applicability can be improved by using long-acting preparations.

Furthermore, the pharmacokinetics was also changed through deuteration. Since another hydrate film is fully formed by deuterated compounds, the distribution of deuterated compounds in organisms is significantly different from that of the non-deuterated compounds.

EXAMPLE 8

The Pharmacodynamic Evaluation of CM4307 for Inhibiting Tumor Growth of Human Heptocellular Carcinoma SMMC-7721 in Nude Mice Xenograft Model 70 Balb/c nu/nu nude mice, 6 weeks-old, female, were bought from Shanghai Experimental Animal Resource Center (Shanghai B&K Universal Group Limited).

SMMC-7721 cells were commercially available from Shanghai Institutes for Biological Science, CAS (Shanghai, China).

The establishment of tumor nude mice xenograft model: SMMC-7721 cells in logarithmic growth period were cultured. After cell number was counted, the cells were suspended in 1×PBS, and the number of the cell in suspension was adjusted to $1.5 \times 10^7$ ml. The tumor cells were inoculated under the skin of right armpit of nude mice with a 1 ml syringe, $3 \times 10^6$/0.2 ml/mice. 70 nude mice were inoculated in total.

When the tumor size reached 30-130 mm$^3$, 58 mice were divided randomly into different groups. The difference of the mean value of tumor volumn in each group was less than 10%, and drugs were started to be administrated.

The test doses for each group were listed in the following table.

| Group | Animal | Compounds | Administration | Dose (mg/kg) | Method |
|---|---|---|---|---|---|
| 1 | 10 | control (solvent) | po | 0.1 ml/10 g BW | qd × 2 weeks |
| 2 | 8 | CM4306 | po | 10 mg/kg | qd × 2 weeks |
| 3 | 8 | CM4306 | po | 30 mg/kg | qd × 2 weeks |
| 4 | 8 | CM4306 | po | 100 mg/kg | qd × 2 weeks |
| 5 | 8 | CM4307 | po | 10 mg/kg | qd × 2 weeks |
| 6 | 8 | CM4307 | po | 30 mg/kg | qd × 2 weeks |
| 7 | 8 | CM4307 | po | 100 mg/kg | qd × 2 weeks |

Animal body weight and tumor size were tested twice a week during the experiment. Clinical symptoms were recorded every day. At the end of the administration, the tumor size was recorded by taking pictures. One mouse was sacrificed in each group and tumor tissue was taken and fixed in 4% paraformaldehyde. Observation was continued after the administration, and when the mean size of tumor was larger than 2000 mm$^3$, or the dying status appeared, the animals were sacrificed, gross anatomy was conducted, and the tumor tissue was taken and fixed in 4% paraformaldehyde.

The formula for calculating the tumor volume (TV) is: TV=a×b$^2$/2, wherein a, b independently represent the length and the breadth of the tumor. The formula for calculating the relative tumor volume (RTV) is: RTV=Vt/V$_0$, wherein V$_0$ is the tumor volume at the beginning of the administration, and Vt is the tumor weight when measured. The index for evaluating the antitumor activity is relative tumor increment rate T/C (%), and the formula is: T/C (%)=(T$_{RTV}$/C$_{RTV}$)×100%, wherein, T$_{RTV}$ is the RTV of the treatment group, and C$_{RTV}$ is the RTV of the negative control group.

Evaluation standard for efficacy: it is effective if the relative tumor increment rate T/C (%) is <40% and p<0.05 by statistics analysis.

Figure 3:
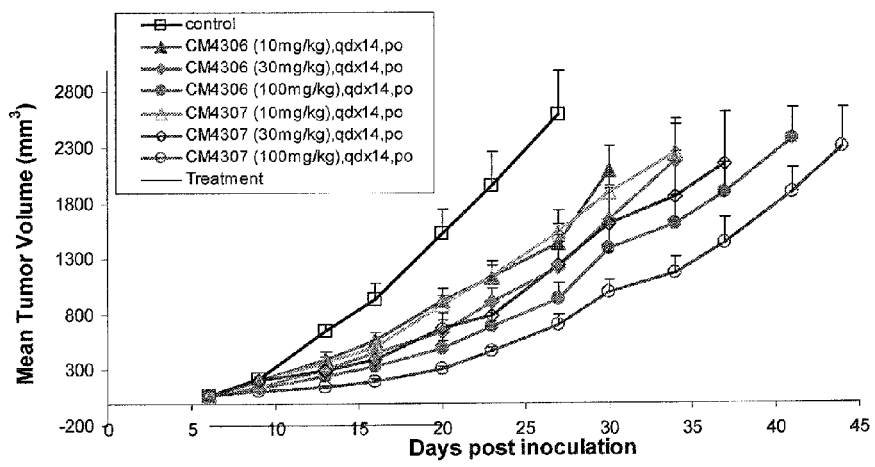
FIG. 3 shows the curves of inhibition efficacy of CM4306 and CM4307 in nude mice xenograft model inoculated with human liver cancer cell SMMC-7721. In this figure, "treatment" means that the treating period was 14 days, followed by the observation period after administration was stopped. The five days before treatment was the period for preparing animal models.

The results were shown in FIG. 3. CM4306 and CM4307 were intragastric administrated every day for 2 weeks at doses of 10, 30, 100 mg/kg respectively, and both compounds showed the dose-dependent effect of the inhibition of tumor growth. At the end of administration, T/C % of CM4306 was 56.9%, 40.6% and 32.2%, respectively. T/C % of CM4307 was 53.6%, 40.8% and 19.6%. T/C % for 100 mg/kg dose groups was <40%, and tumor volume was significantly different (p<0.01) from the control group, indicating the significant effect in inhibiting tumor growth.

Compared with CM4306, the inhibitory efficacy of tumor growth at dosing 100 mg/kg of CM4307 was stronger (the T/C % for CM4307 and CM4306 is 19.6% and 32.2%, respectively, at day 15), there was significant difference in tumor volume between groups (p<0.01). Compared with CM4306, the absolute value of tumor inhibition rate for CM4307 increased more than 10%, the relative value increment about 60% (32.2%/19.6%−1=64%), and CM4307 showed more significant effect for inhibiting tumor growth.

In addition, during the experiment, no other drug-relevant toxic effects were observed.

EXAMPLE 9

Pharmaceutical Compositions

| | |
|---|---|
| Compound CM4307 (Example 1) | 20 g |
| Starch | 140 g |
| Microcrystalline cellulose | 60 g |

By routine methods, these substances were blended evenly, and loaded into ordinary gelatin capsules, thereby forming 1000 capsules.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

What is claimed is:
1. A method for preparing a compound, N-(4-chloro-3-(trifluoromethyl)phenyl)-N'-(4-(2-(N-(methyl-d$_3$)aminoformyl)-4-pyridyloxy)phenyl)urea:

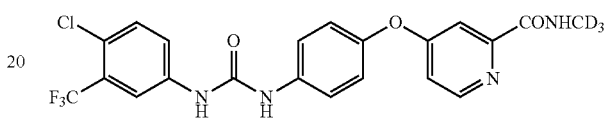

comprising a step selected from the group consisting of (a), (b) and (c):
(a) in an inert solvent and in the presence of a base, reacting compound III with compound V to form the compound:

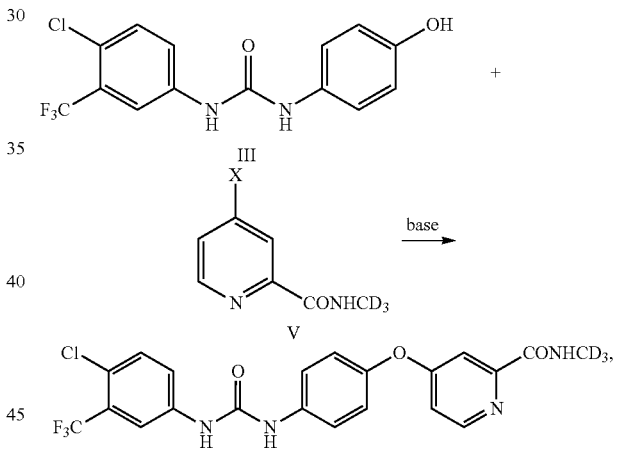

wherein X is Cl, Br, or I; and
the compound III is prepared using a method comprising:
(i) reacting p-methoxy-aniline (X) with 4-chloro-3-trifluoromethyl-aniline (II) or 4-chloro-3-trifluoromethyl phenyl isocyanate (VIII) to form compound XI:

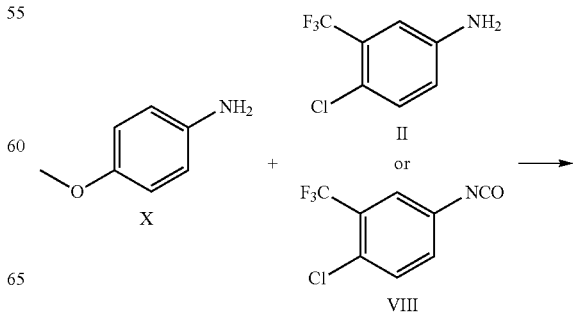

-continued

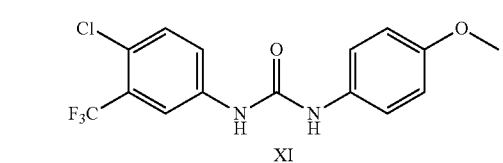

and (ii) in an acidic or basic condition, demethylating compound XI to form compound III;

(b) in an inert solvent, reacting compound IX with CD₃NH₂ or CD₃NH₂.HCl to form the compound:

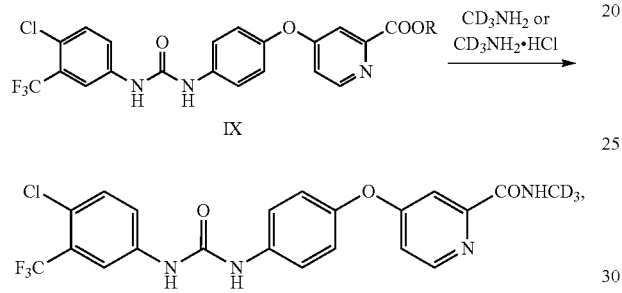

wherein R is a straight-chain or branched chain C1-C8 alkyl, or aryl; and (c) in an inert solvent, reacting 4-chloro-3-trifluoromethyl phenyl isocyanate (VIII) with compound 5 to form the compound, wherein the inert solvent is the mixed solvent of dimethylsulfoxide and dichloromethane:

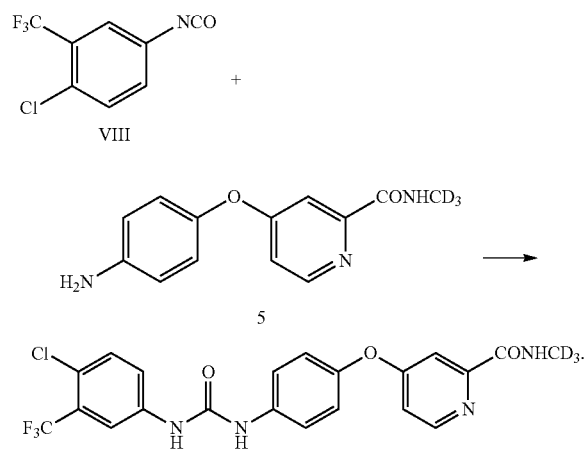

2. The method according to claim 1, wherein the compound IX is prepared using a method comprising reacting compound VII with compound II or compound VIII to form the compound IX:

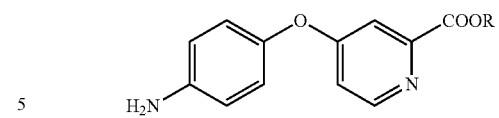

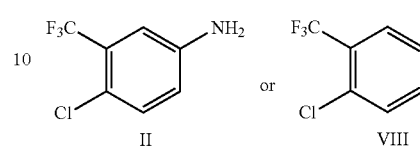

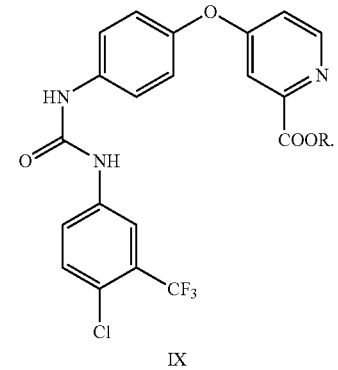

3. The method according to claim 2, wherein the compound VII is prepared using a method comprising, in the presence of a base, reacting compound VI and p-hydroxyl-aniline to form the compound VII:

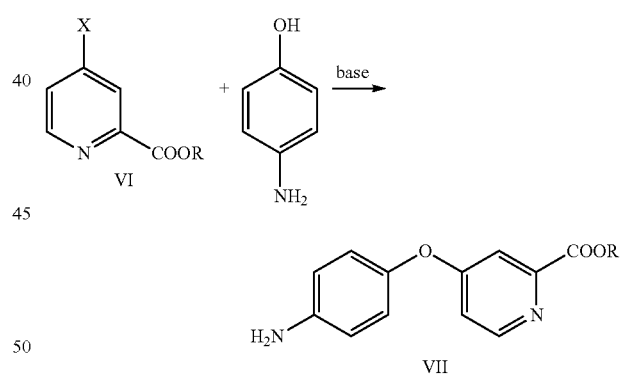

wherein X is chlorine, bromine or iodine; and R is a straight-chain or branched chain C1-C8 alkyl, or aryl.

4. The method according to claim 1, wherein the base is selected from the group consisting of potassium tert-butoxide, sodium hydride, potassium hydride, potassium carbonate, cesium carbonate, potassium phosphate, potassium hydroxide, sodium hydroxide and the combination thereof.

5. A method for preparing 4-chloro-pyridyl-2-(N-(methyl-d₃))carboxamide, comprising:

(a1) under a basic condition and in an inert solvent, reacting methyl 4-chloro-2-pyridyl-formate with (methyl-d₃) amine or a salt thereof to form 4-chloro-pyridyl-2-(N-(methyl-d₃))carboxamide.

6. A method of preparing a deuterated ω-diphenylurea, comprising using
an intermediate of formula B:
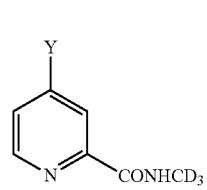
(B)
in the preparation, wherein Y is a halogen or
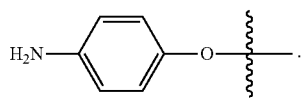
7. The method according to claim 6, wherein the deuterated ω-diphenylurea is 4-(4-(3-(4-chloro-3-(trifluoromethyl)phenyl]ureido)-phenoxy)-N-(methyl-$d_3$)picolinamide p-toluenesulfonate.
* * * * *